(12) United States Patent
Sasai et al.

(10) Patent No.: US 10,760,047 B2
(45) Date of Patent: Sep. 1, 2020

(54) METHOD FOR PRODUCING ADENOHYPOPHYSIS OR PRECURSOR TISSUE THEREOF

(71) Applicants: RIKEN, Wako-shi, Saitama (JP); SUMITOMO CHEMICAL COMPANY, LIMITED, Tokyo (JP)

(72) Inventors: Yoshiki Sasai, Wako (JP); Chikafumi Ozone, Wako (JP); Hidetaka Suga, Wako (JP)

(73) Assignees: RIKEN, Wako (JP); SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/328,985

(22) PCT Filed: Jul. 24, 2015

(86) PCT No.: PCT/JP2015/071150
§ 371 (c)(1),
(2) Date: Jan. 25, 2017

(87) PCT Pub. No.: WO2016/013669
PCT Pub. Date: Jan. 28, 2016

(65) Prior Publication Data
US 2018/0195041 A1 Jul. 12, 2018

(30) Foreign Application Priority Data

Jul. 25, 2014 (JP) .................................. 2014-152384

(51) Int. Cl.
| | |
|---|---|
| *C12N 5/00* | (2006.01) |
| *C12N 5/02* | (2006.01) |
| *C12N 5/079* | (2010.01) |
| *C12N 5/0735* | (2010.01) |

(52) U.S. Cl.
CPC ......... *C12N 5/0618* (2013.01); *C12N 5/0031* (2013.01); *C12N 5/0037* (2013.01); *C12N 5/0606* (2013.01); *C12N 2501/115* (2013.01); *C12N 2501/41* (2013.01); *C12N 2501/42* (2013.01)

(58) Field of Classification Search
CPC .. C12N 5/0618; C12N 5/0031; C12N 5/0037; C12N 5/0606; C12N 2501/115; C12N 2501/41; C12N 2501/42
See application file for complete search history.

(56) References Cited

U.S. PATENT DOCUMENTS

2014/0308743 A1   10/2014  Sasai et al.

FOREIGN PATENT DOCUMENTS

| JP | 2013-128476 A | 7/2013 |
|---|---|---|
| WO | WO 2013/065763 A1 | 5/2013 |
| WO | WO 2013/166488 A1 | 11/2013 |
| WO | WO 2015/077648 A1 | 5/2015 |

OTHER PUBLICATIONS

Dincer et al., "Specification of Functional Cranial Placode Derivatives from Human Pluripotent Stem Cells," *Cell Rep.*, 5(5): 1387-1402 (2013).
Gospodarowicz et al., "Fibroblast Growth Factor and the Control of Pituitary and Gonad Development and Function," *J. Steroid Biochem.*, 32(1B): 183-191 (1989).
Iwai-Liao et al., "Immunohistochemical Localization of Certain Inducers Related to the Proliferation of the Pituitary Gland and a Study on Cell Contacts between the Presumptive Neurohypophysis and the Adenohypophysis in the Foetal Mouse," *Okajimas Folia Anat. Jpn.*, 77(4): 109-118 (2000).
Leung et al., "Differential BMP signaling controls formation and differentiation of multipotent preplacodal ectoderm progenitors from human embryonic stem cells," *Dev. Biol.*, 379(2): 208-220 (2013).
Sasai, "Sohatsu Seibutsugaku eno Sasoi Shinpi no Veil ni Kakusareta Seimei Rashisa ni Idomu Dai 2 Kai Tasaibo Shakai ni Miru Jiko Soshikika: Ganpai nado no Jiko Soshikika o Rei ni," *Experimental Medicine*, 31(16): 2645-2652 (2013).
Sasai, "Shinkeikei Soshiki no Pattern Keisei ni Miru Jiko Soshikika: Sohatsu Seibutsugaku eno Chosen," *Brain Science Review*, 2014: 99-112 (2014).
Suga et al., "Self-formation of functional adenohypophysis in three-dimensional culture," *Nature*, 480(7375): 57-62 (2011).
Suga et al., "Self-Formation of Adenohypophysis from Mouse Embryonic Stem Cells," *Gendai Igaku*, 61(2): 191-199 (2013).
Wang et al., "Direct and indirect requirements of Shh/Gli signaling in early pituitary development," *Dev. Biol.*, 348: 199-209 (2010).
Wataya et al., "Minimization of exogenous signals in ES cell culture induces rostral hypothalamic differentiation," *Proc. Natl. Acad. Sci. U.S.A.*, 105(33): 11796-11801 (2008).
Japanese Patent Office, International Search Report in International Patent Application No. PCT/JP2015/071150 (dated Oct. 27, 2015).
Japanese Patent Office, Written Opinion in International Patent Application No. PCT/JP2015/071150 (dated Oct. 27, 2015).

*Primary Examiner* — Valarie E Bertoglio
(74) *Attorney, Agent, or Firm* — Leydig, Voit & Mayer, Ltd.

(57) ABSTRACT

The present invention provides a method for inducing adenohypophysis or precursor tissue thereof in vitro from human pluripotent stem cells. The method includes culturing an aggregate of human pluripotent stem cells in suspension in a medium containing a bone morphogenetic protein signal transduction pathway activating substance and a substance acting on the Shh signal pathway to obtain a human cell aggregate containing a hypothalamus neuroepithelial tissue and a surface ectoderm, and further culturing the obtained human cell aggregate containing the hypothalamus neuroepithelial tissue and the surface ectoderm in suspension in a medium containing a bone morphogenetic protein signal transduction pathway activating substance and a substance acting on the Shh signal pathway to induce formation of hypophysial placode and/or Rathke's pouch in the surface ectoderm, thus obtaining a human cell aggregate containing 1) hypothalamus neuroepithelial tissue, and 2) hypophysial placode and/or Rathke's pouch.

19 Claims, 11 Drawing Sheets

METHOD FOR PRODUCING ADENOHYPOPHYSIS OR PRECURSOR TISSUE THEREOF

CROSS-REFERENCE TO RELATED APPLICATIONS

This patent application is the U.S. national phase of International Patent Application No. PCT/JP2015/071150, filed on Jul. 24, 2015, which claims the benefit of Japanese Patent Application No. 2014-152384, filed on Jul. 25, 2014, the disclosures of which are incorporated herein by reference in their entireties for all purposes.

TECHNICAL FIELD

The present invention relates to a technique for inducing differentiation of pluripotent stem cells into an adenohypophysis or a progenitor tissue thereof in vitro.

BACKGROUND ART

Hypophysis is a small endocrine organ adjacent to the lower part of the diencephalon and plays a major role as a control center of various hormones. For example, it produces various pituitary hormones including adrenocorticotropic hormone (ACTH) which promotes production of corticosteroid essential for life support, growth hormone which promotes growth of children, and the like. Therefore, functional disorder of hypophysis causes severe systemic diseases. However, since hypophysis is formed through an extremely complicated developmental process in the embryo, it has been difficult to form hypophysis tissue from stem cells such as Embryonic Stem (ES) cells and the like.

The present inventors applied Serum-free Floating culture of Embryoid Body-like aggregates with quick reaggregation (SFEBq method) established as a method for efficiently differentiate nerve cells and retinal cells from pluripotent stem cells such as ES cells and the like, and succeeded in self-organization of the hypophysis from mouse ES cells in vitro (non-patent document 1). In this method, hedgehog signal is activated by culturing aggregates of mouse ES cells in suspension in a serum-free medium containing SAG, and hypothalamus and oral ectoderm are simultaneously formed in the aggregates, and the interaction thereof induces hypophysial placode formation and self organization of Rathke's pouch. It has been reported that endogenous BMP4 signal is required for hypophysial placode formation in this method based on inhibition experiments.

DOCUMENT LIST

Non-Patent Document non-patent document 1: Nature. 2011 Nov. 9; 480(7375): 57-62

SUMMARY OF THE INVENTION

Problems to be Solved by the Invention

Aiming at self organization of hypophysis from human pluripotent stem cells, the present inventors applied the above-mentioned method to human pluripotent stem cells. However, they could not achieve efficient hypophysis formation as in mouse.

Therefore, the present invention aims to provide a technique for efficiently inducing adenohypophysis or precursor tissue thereof from human pluripotent stem cells in vitro.

Means of Solving the Problems

Firstly, the present inventors added BMP4 exogenously to a mouse system, and verified the effect thereof. However, in the mouse system, although addition of the exogenous BMP4 signal promoted formation of surface ectoderm, it rather acted inhibitingly on the formation of the neuroepithelial tissue (hypothalamus) inside the cell aggregate and it was difficult to form a cell aggregate including both surface ectoderm and hypothalamic neuroepithelial tissue. However, it was unexpectedly found that, in a system using human pluripotent stem cells, unlike mice, exogenous BMP4 promotes both formation of surface ectoderm on the surface and formation of hypothalamus neuroepithelial tissue in the inside. When aggregates of human pluripotent stem cells cultured in suspension in a medium containing BMP4 and SAG, both hypothalamic neuroepithelial tissue and surface ectoderm were simultaneously formed in the cell aggregates, and the hypophysial placode was formed in the surface ectoderm by their interaction. The hypophysial placode invaginated into the inside, and formed a Rathke's pouch-like sac structure. Continuous cultivation resulted in the emergence of ACTH-producing cells, GH-producing cells and PRL-producing cells in the hypophysial placode and Rathke's pouch. The cell aggregates containing hypophysial placode or Rathke's pouch secreted ACTH in response to CRH stimulation, and the ACTH secretion was suppressed in a feedback manner by glucocorticoid. Therefore, it was shown that the cell aggregates had the ability to control secretion of pituitary hormone in response to stimulation of the hypothalamus and feedback regulation from the downstream target tissue, in the same manner as with the hypophysis in the body.

The present inventors have conducted further studies based on the above-mentioned findings and completed the present invention.

Accordingly, the present invention is as follows:

[1] A method for producing a human cell aggregate comprising adenohypophysis or a precursor tissue thereof, which comprises culturing an aggregate of human pluripotent stem cells in suspension in a medium containing a bone morphogenetic protein signal transduction pathway activating substance and a substance acting on the Shh signal pathway.

[2] The production method of [1], comprising culturing an aggregate of human pluripotent stem cells in suspension in a medium containing a bone morphogenetic protein signal transduction pathway activating substance and a substance acting on the Shh signal pathway to obtain a human cell aggregate comprising a hypothalamus neuroepithelial tissue and a surface ectoderm by, and further culturing the obtained human cell aggregate comprising the hypothalamus neuroepithelial tissue and the surface ectoderm in suspension in a medium containing a bone morphogenetic protein signal transduction pathway activating substance and a substance acting on the Shh signal pathway to induce formation of hypophysial placode and/or Rathke's pouch in the surface ectoderm, thereby obtaining a human cell aggregate comprising 1) hypothalamic neuroepithelial tissue, and 2) hypophysial placode and/or Rathke's pouch.

[3] The production method of [2], wherein the medium used for the further culturing in suspension further comprises FGF2.

[4] The production method of [2] or [3], which comprises further culturing the human cell aggregate comprising 1) hypothalamus neuroepithelial tissue, and 2) hypophysial placode and/or Rathke's pouch in suspension in a medium comprising a substance acting on the Shh signal pathway to induce differentiation of hypophysial placode and/or Rathke's pouch into pituitary hormone-producing cells, thereby obtaining a human cell aggregate comprising adenohypophysis.

[5] The production method of [4], wherein the medium used for the further culturing in suspension further comprises FGF2.

[6] The production method of [4] or [5], wherein the medium used for the further culturing in suspension further comprises a Notch signal inhibitor.

[7] The production method of [6], wherein the Notch signal inhibitor is DAPT.

[8] The production method of any of [4]-[7], wherein the pituitary hormone-producing cell is at least one selected from the group consisting of growth hormone (GH)-producing cell, prolactin (PRL)-producing cell, and adrenocorticotropic hormone (ACTH)-producing cell.

[9] The production method of any of [1]-[8], wherein the bone morphogenetic protein signal transduction pathway activating substance is BMP4.

[10] The production method of any of [1]-[9], wherein the substance acting on the Shh signal pathway is SAG.

[11] The production method of any of [1]-[10], wherein the hypothalamus neuroepithelial tissue is a ventral hypothalamus neuroepithelial tissue.

[12] The production method of any of [1]-[11], wherein the pluripotent stem cells are embryonic stem cells or induced pluripotent stem cells.

[13] The production method of any of [1]-[12], wherein the suspension culture is performed in the absence of feeder cells.

[14] A cell aggregate obtainable by the production method of any of [1]-[13].

Effect of the Invention

According to the present invention, adenohypophysis or a precursor tissue thereof can be efficiently induced from human pluripotent stem cells in vitro. Both the hypothalamus neuroepithelial tissue and surface ectoderm are simultaneously formed in the aggregate of human pluripotent stem cells, and hypophysial placode and Rathke's pouch are self organized by the interactions thereof. According to the present invention, in the same manner as the hypophysis in a body, human adenohypophysis having an ability to regulate secretion of pituitary hormone in response to stimulation of the hypothalamus and feedback regulation from the downstream target tissue can be constructed in vitro.

Figure 1:
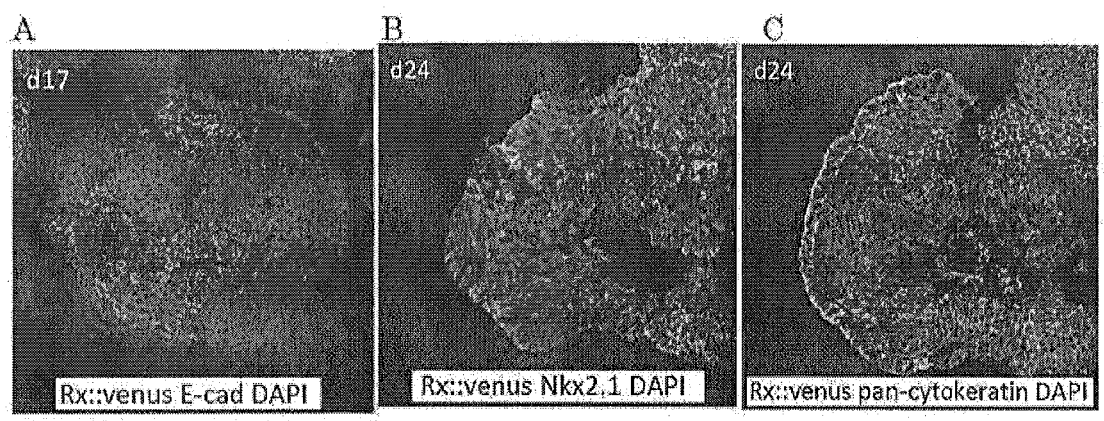
FIG. 1 shows three dimensional formation of ventral hypothalamus and epidermal placode from human pluripotent stem cells. A: d17 aggregate. Rx::Venus: green, E-cadherin: red, DAPI: blue. B: d24 aggregate. Rx::Venus: green, Nkx2.1: red, DAPI: blue. C: d24 aggregate. Rx::Venus: green, pan-cytokeratin: white, DAPI: blue.

DESCRIPTION OF EMBODIMENTS (1) Pluripotent Stem Cell

The "pluripotent stem cell" refers to a cell having both the potential for differentiating into all cells constituting the body (pluripotency), and the potential for producing daughter cells having the same differentiation potency via cell division (self-replication competence).

The pluripotency can be evaluated by transplanting the cells of an evaluation subject into a nude mouse, and testing the presence or absence of formation of teratoma containing each cell of three germ layers (ectoderm, mesoderm, endoderm).

Examples of the pluripotent stem cell include embryonic stem cell (ES cell), embryonic germ cell (EG cell), induced pluripotent stem cell (iPS cell) and the like, and the pluripotent stem cell is not limited as long as it has both the pluripotency and the self-replication competence. In the present invention, embryonic stem cells or induced pluripotent stem cells are preferably used.

Embryonic stem cells (ES cell) can be established by culturing, for example, a pre-implantation early embryo, an inner cell mass that constitutes the early embryo, a single blastomere and the like (Manipulating the Mouse Embryo A Laboratory Manual, Second Edition, Cold Spring Harbor Laboratory Press (1994); Thomson, J. A. et al., Science, 282, 1145-1147 (1998)). As the early embryo, an early embryo prepared by nuclear-transplanting the nucleus of a somatic cell may be used (Wilmut et al. (Nature, 385, 810 (1997)), Cibelli et al. (Science, 280, 1256 (1998)), Akira IRITANI et al. (Tanpakushitsu Kakusan Koso, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000), Tachibana et al. (Human Embryonic Stem Cells Derived by Somatic Cell Nuclear Transfer, Cell (2013) in press)). As an early embryo, a parthenogenetic embryo may also be used (Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008)).

Fused ES cell obtained by cell fusion of ES cell and somatic cell is also included in the embryonic stem cells used for the method of the present invention.

Embryonic stem cells are available from appropriate organizations, and commercial products may be purchased. For example, the human embryonic stem cells KhES-1, KhES-2 and KhES-3 are available from the Institute for Frontier Medical Sciences, Kyoto University.

Embryonic germ cells (EG cell) can be established by culturing primordial germ cells in the presence of LIF, bFGF, SCF and the like (Matsui et al., Cell, 70, 841-847 (1992), Shamblott et al., Proc. Natl. Acad. Sci. USA, 95(23), 13726-13731 (1998), Turnpenny et al., Stem Cells, 21(5), 598-609, (2003)).

Induced pluripotent stem cell (iPS cell) refers to a cell that artificially acquired pluripotency and self-replication competence by contacting a somatic cell (e.g., fibroblast, skin cell, lymphocyte etc.) with a nuclear reprogramming factor. iPS cell was found for the first time by a method comprising introducing nuclear reprogramming factors composed of Oct3/4, Sox2, Klf4 and c-Myc into somatic cells (e.g., fibroblast, skin cell etc.) (Cell, 126: p. 663-676, 2006). Thereafter, many researchers have made various improvements in the combination of reprogramming factors and introduction method of the factors, and various production methods of induced pluripotent stem cell have been reported.

The nuclear reprogramming factors may be configured with any substance, such as a proteinous factor or a nucleic acid that encodes the same (including forms incorporated in a vector), or a low molecular compound, as long as it is a substance (substances) capable of inducing a cell having pluripotency and self-replication competence from a somatic cell such as fibroblast and the like. When the nuclear reprogramming factor is a proteinous factor or a nucleic acid that encodes the same, preferable nuclear reprogramming factors are exemplified by the following combinations (hereinafter, only the names for proteinous factors are shown).

(1) Oct3/4, Klf4, Sox2, c-Myc (wherein Sox2 is replaceable with Sox1, Sox3, Sox15, Sox17 or Sox18. Klf4 is replaceable with Klf1, Klf2 or Klf5. Furthermore, c-Myc is replaceable with T58A (active form mutant), N-Myc or L-Myc.)
(2) Oct3/4, Klf4, Sox2
(3) Oct3/4, Klf4, c-Myc
(4) Oct3/4, Sox2, Nanog, Lin28
(5) Oct3/4, Klf4, c-Myc, Sox2, Nanog, Lin28
(6) Oct3/4, Klf4, Sox2, bFGF
(7) Oct3/4, Klf4, Sox2, SCF
(8) Oct3/4, Klf4, c-Myc, Sox2, bFGF
(9) Oct3/4, Klf4, c-Myc, Sox2, SCF Among these combinations, when use of the obtained iPS cell for therapeutic application is considered, a combination of the three factors of Oct3/4, Sox2 and Klf4 is preferable. On the other hand, when use of the iPS cell for therapeutic application is not considered (e.g., used as an investigational tool for drug discovery screening and the like), four factors consisting of Oct3/4, Klf4, Sox2 and c-Myc, or 5 factors by adding Lin28 or Nanog thereto are preferable.

An iPS cell is preferably used for autologous transplantation.

A pluripotent stem cell obtained by modifying genes in a chromosome by a known genetic engineering method can also be used in the present invention. The pluripotent stem cell may be a cell wherein a labeling gene (e.g., fluorescent protein such as GFP etc.) has been knocked in a gene encoding a differentiation marker in an in-frame manner by a known method, which cell can be identified to have reached the corresponding differentiation stage by using the expression of the labeling gene as an index.

As the pluripotent stem cell, warm-blooded animal pluripotent stem cells, preferably mammalian pluripotent stem cells, can be used. Mammals include, for example, laboratory animals, including rodents such as mice, rats, hamsters and guinea pigs, and rabbits; domestic animals such as pigs, cattle, goat, horses, and sheep; companion animals such as dogs and cats; primates such as humans, monkeys, orangutans, and chimpanzees. Pluripotent stem cell is preferably pluripotent stem cell of rodents (mouse, rat etc.) or primates (human etc.) and most preferably human pluripotent stem cell.

Pluripotent stem cells can be cultured for maintenance by a method known per se. For example, from the aspects of clinical application, pluripotent stem cells are preferably maintained by serum-free culture using serum alternatives such as Knockout™ Serum Replacement (KSR) and the like, or feeder-free cell culture.

The pluripotent stem cells to be used in the present invention are preferably isolated. Being "isolated" means that an operation to remove factors other than the target cell or component has been performed, and the cell or component is no longer in a natural state. The purity of the "isolated human pluripotent stem cells" (percentage of the number of human pluripotent stem cells to the total cell number) is generally not less than 70%, preferably not less than 80%, more preferably not less than 90%, further preferably not less than 99%, most preferably 100%.

(2) Formation of Pluripotent Stem Cell Aggregate

An aggregate of pluripotent stem cells can be obtained by culturing dispersed pluripotent stem cells under conditions that are non-adhesive to the culture vessel (i.e., culturing in suspension), and assembling plural pluripotent stem cells to allow for aggregate formation.

A culture vessel used for the aggregate formation is not particularly limited, and examples thereof include flasks, tissue culture flasks, dishes, Petri dishes, tissue culture dishes, multi-dishes, microplates, micro-well plates, micropores, multi-plates, multi-well plates, chamber slides, bowls, tubes, trays, culture bags, and roller bottles. To enable culture under non-adhesive conditions, the culture vessel is preferably non-cell-adherent. Useful non-cell-adherent culture vessels include culture vessels whose surfaces have been artificially treated to be cell non-adherent, culture vessels whose surfaces have not undergone an artificial treatment for improving the cell adhesiveness (e.g., coating treatment with an extracellular matrix and the like), and the like.

The medium to be used for aggregate formation can be prepared using a medium used for culturing mammalian cells as a basal medium. The basal medium is not particularly limited as long as it can be used for culture of mammalian cells and may be BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, Ham's F-12 medium, RPMI 1640 medium, Fischer's medium, Neurobasal medium, a mixed medium thereof and the like. In one embodiment, a mixed medium of IMDM medium and Ham's F-12 medium is used. The mixing ratio is, for example, IMDM:Ham's F-12=0.8-1.2:1.2-0.8, in a volume ratio.

The medium to be used for culture may be a serum-containing medium or a serum-free medium. The serum-free medium means a medium free of an unadjusted or unpurified serum. A medium containing purified components derived from blood and components derived from animal tissue (e.g., growth factor) corresponds to a serum-free medium. To avoid contamination with chemically-undefined components, a serum-free medium is preferably used in the present invention.

The medium to be used for aggregate formation may contain a serum alternative. The serum alternative can, for example, be one comprising as appropriate albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of the method of the present invention, commercially available serum alternatives can be utilized. Examples of such commercially available serum alternatives include Knockout Serum Replacement (KSR, produced by Invitrogen), Chemically-defined Lipid Concentrated (produced by Gibco Company) and Glutamax (produced by Gibco Company).

A medium to be used for aggregate formation can contain other additive as long as induction of differentiation of pluripotent stem cells into hypophysis or a partial tissue thereof, or a precursor tissue thereof is not adversely influenced. Examples of the additive include, but are not limited to, insulin, iron source (e.g., transferrin etc.), minerals (e.g., sodium selenate etc.), saccharides (e.g., glucose etc.), organic acids (e.g., pyruvic acid, lactic acid etc.), serum proteins (e.g., albumin etc.), amino acids (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

A medium to be used for aggregate formation may be a medium used in the below-mentioned first culture step.

For formation of an aggregate of pluripotent stem cells, pluripotent stem cells are collected from passage culture and dispersed to a single cell state or near single cell state. Pluripotent stem cells are dispersed with an appropriate cell dissociation solution. Examples of the cell dissociation solution include EDTA; protease such as trypsin, collagenase IV, and metalloproteinase, and the like, which can be used alone or in an appropriate combination. Of these, one showing low cell toxicity is preferable, and examples of such cell dissociation solution include commercially available products such as DISPASE (EIDIA), TrypLE (Invitrogen), Accutase (MILLIPORE) and the like. The dispersed pluripotent stem cells are suspended in the above-mentioned medium.

To suppress cell death of pluripotent stem cells (particularly, human pluripotent stem cells) induced by dispersion, it is preferable to add an inhibitor of Rho-associated coiled-coil kinase (ROCK) from the start of cultivation (JP-A-2008-99662). A ROCK inhibitor is added for, for example, within 15 days, preferably within 10 days, more preferably within 6 days, from the start of the culture. Examples of the ROCK inhibitor include Y-27632 ((+)-(R)-trans-4-(1-aminoethyl)-N-(4-pyridyl)cyclohexanecarboxamide dihydrochloride) and the like. The concentration of the ROCK inhibitor used for suspension culture is a concentration capable of suppressing cell death of pluripotent stem cells induced by dispersion. For example, for Y-27632, this concentration is normally about 0.1 to 200 µM, preferably about 2 to 50 µM. The concentration of the ROCK inhibitor may be changed in the addition period thereof and, for example, the concentration may be reduced to half in the latter half period.

A suspension of the dispersed pluripotent stem cells is seeded in the above-mentioned culture vessel and the dispersed pluripotent stem cells are cultured under conditions that are non-adhesive to the cell culture vessel, whereby the plural pluripotent stem cells are assembled to form an aggregate. In this case, dispersed pluripotent stem cells may be seeded in a comparatively large culture vessel such as a 10-cm dish to simultaneously form plural pluripotent stem cell aggregates in one culture compartment. However, the size of aggregates, and the number of pluripotent stem cells contained therein may vary widely, and such variation may cause difference in the levels of differentiation of pluripotent stem cells into hypophysis or a partial tissue thereof, or a precursor tissue thereof between aggregates, which in turn may lower the efficiency of differentiation induction. Therefore, it is preferable to rapidly coagulate the dispersed pluripotent stem cells to form one aggregate in one culture compartment. Examples of the method for rapidly coagulating the dispersed pluripotent stem cells include the following methods:

(1) A method including enclosing dispersed pluripotent stem cells in a culture compartment having a comparatively small volume (e.g., not more than 1 ml, not more than 500 μl, not more than 200 μl, not more than 100 μl) to form one aggregate in the compartment. Preferably, the culture compartment is stood still after enclosing the dispersed pluripotent stem cells. Examples of the culture compartment include, but are not limited to, a well in a multi-well plate (384-well, 192-well, 96-well, 48-well, 24-well etc.), micropore, chamber slide and the like, tube, a droplet of a medium in hanging drop method and the like. The dispersed pluripotent stem cells enclosed in the compartment are precipitated on one spot due to the gravity, or the cells adhere to each other to form one aggregate in one culture compartment. The shape of the bottom of the multiwall plate, micropore, chamber slide, tube and the like is preferably U-bottom or V-bottom to facilitate precipitation of the dispersed pluripotent stem cells on one spot.

(2) A method including placing dispersed pluripotent stem cells in a centrifugation tube, centrifuging same to allow for precipitation of pluripotent stem cells on one spot, thereby forming one aggregate in the tube.

The number of pluripotent stem cells to be seeded in one culture compartment is not particularly limited as long as one aggregate is formed per one culture compartment, and differentiation of pluripotent stem cells into hypophysis or a partial tissue thereof, or a precursor tissue thereof can be induced in the aggregate by the method of the present invention. Generally, about $1 \times 10^3$-about $5 \times 10^4$, preferably about $1 \times 10^3$-about $2 \times 10^4$, more preferably about $2 \times 10^3$-about $1.2 \times 10^4$ of pluripotent stem cells are seeded in one culture compartment. Then, by rapidly coagulating the pluripotent stem cells, one cell aggregate generally composed of about $1 \times 10^3$-about $5 \times 10^4$, preferably about $1 \times 10^3$-about $2 \times 10^4$, more preferably about $2 \times 10^3$-about $1.2 \times 10^4$ pluripotent stem cells is formed per one culture compartment.

The time up to aggregate formation can be determined as appropriate as long as one aggregate is formed per one compartment, and differentiation of pluripotent stem cells into hypophysis or a partial tissue thereof, or a precursor tissue thereof can be induced in the aggregate by the method of the present invention. By shortening the time, efficient induction of differentiation into the object hypophysis or a partial tissue thereof or a precursor tissue thereof is expected, and therefore, said time is preferably shorter. Preferably, pluripotent stem cell aggregate is formed within 24 hr, more preferably within 12 hr, further preferably within 6 hr, most preferably in 2-3 hr. The time up to the aggregate formation can be adjusted as appropriate by choosing a tool for cell aggregation, centrifugal conditions and the like by those skilled in the art.

Other culturing conditions such as culturing temperature and $CO_2$ concentration at the time of aggregate formation can be set as appropriate. The culturing temperature is not particularly limited, and is, for example, about 30 to 40° C., preferably about 37° C. The $CO_2$ concentration is, for example, about 1 to 10%, preferably about 5%.

Furthermore, plural culture compartments under the same culture conditions are prepared and one pluripotent stem cell aggregate is formed in each culture compartment, whereby a qualitatively uniform population of aggregates of pluripotent stem cell aggregates can be obtained. Whether pluripotent stem cell aggregates are qualitatively uniform can be evaluated on the basis of the size of the aggregate mass and the number of cells therein, macroscopic morphology, microscopic morphology and homogeneity thereof as analyzed by histological staining, the expression of differentiation and un-differentiation markers and homogeneity thereof, the regulation of the expression of differentiation markers and synchronicity thereof, reproducibility of differentiation efficiency among aggregates, and the like. In one embodiment, a population of the aggregates of pluripotent stem cells to be used in the method of the present invention contains a uniform number of pluripotent stem cells in the aggregates. A population of aggregates of pluripotent stem cells being "uniform" in a particular parameter means that not less than 90% of the total aggregates in a population thereof falls within the range of mean of the parameter in the aggregate population ±10%, preferably ±5%.

(3) Induction of Adenohypophysis or Precursor Tissue Thereof

The present invention provides a method for producing a cell aggregate comprising adenohypophysis or a progenitor tissue thereof, comprising culturing an aggregate of pluripotent stem cells in suspension in a medium containing a bone morphogenetic protein signal transduction pathway activating substance and a substance acting on the Sonic hedgehog (Shh) signal pathway.

In the present invention, adenohypophysis refers to a tissue containing at least one kind of anterior or intermediate pituitary hormone-producing cell. Examples of the pituitary hormone-producing cell include cells constituting the anterior such as growth hormone (GH)-producing cells, prolactin (PRL)-producing cells, adrenocorticotropic hormone (ACTH)-producing cells, thyroid-stimulating hormone (TSH)-producing cells, follicle-stimulating hormone (FSH)-producing cells, luteinizing hormone (LH)-producing cells and the like; and cells constituting the intermediate such as melanocyte-stimulating hormone (MSH)-producing cells and the like. In one embodiment, adenohypophysis contains at least one kind, preferably two kinds, more preferably three kinds, of pituitary hormone-producing cells selected from the group consisting of growth hormone (GH)-producing cells, prolactin (PRL)-producing cells, and adrenocorticotropic hormone (ACTH)-producing cells. In a further embodiment, adenohypophysis contains at least one kind, preferably two or more kinds (2, 3, 4, 5 or 6 kinds), of pituitary hormone-producing cells selected from the group consisting of growth hormone (GH)-producing cells, prolactin (PRL)-producing cells, adrenocorticotropic hormone (ACTH)-producing cells, thyroid-stimulating hormone (TSH)-producing cells, follicle-stimulating hormone (FSH)-producing cells, and luteinizing hormone (LH)-producing cells.

In the present invention, tissue refers to a structure of a cell population having a structure in which plural kinds of cells having different forms and properties are sterically arranged in a certain pattern.

As a precursor tissue of adenohypophysis, hypophysial placode, Rathke's pouch and the like can be mentioned. The hypophysial placode is a thickened structure formed in the surface ectoderm region in the process of embryogenic development and expresses a hypophysis progenitor cell marker. As a hypophysis progenitor cell marker, Lim3, Pitx1, Isl1/2 and the like can be mentioned. The hypophysial placode expresses at least one, preferably all, hypophysis progenitor cell markers selected from the group consisting of Lim3, Pitx1 and Isl1/2. Rathke's pouch refers to a sac structure formed by the invagination of the hypophysial placode.

The production method of the present invention specifically comprises culturing an aggregate of pluripotent stem cells in suspension in a medium containing a bone morphogenetic protein signal transduction pathway activating substance and a substance acting on the Shh signal pathway to obtain a cell aggregate comprising a hypothalamus neuroepithelial tissue and a surface ectoderm (first culture step), and further culturing the obtained cell aggregate comprising the hypothalamus neuroepithelial tissue and the surface ectoderm in suspension in a medium containing a bone morphogenetic protein signal transduction pathway activating substance and a substance acting on the Shh signal pathway to obtain a cell aggregate comprising 1) hypothalamus neuroepithelial tissue, and 2) hypophysial placode and/or Rathke's pouch (second culture step). The first culture step induces differentiation of the hypothalamus neuroepithelial tissue and surface ectoderm from the pluripotent stem cells and, by subjecting the cell aggregate containing the hypothalamus neuroepithelial tissue and surface ectoderm to the second culture step, further differentiation of the surface ectoderm into hypophysial placode and/or Rathke's pouch is induced.

(3.1) First Culture Step

In the first culture step, an aggregate of pluripotent stem cells is cultured in suspension in a medium containing a bone morphogenetic protein signal transduction pathway activating substance and a substance acting on the Shh signal pathway.

"Culturing in suspension" of a pluripotent stem cell aggregate refers to culturing an aggregate of pluripotent stem cells in a medium under conditions that are non-adhesive to the culture vessel. This enables efficient induction of adenohypophysis or precursor tissue thereof which was conventionally difficult.

A medium to be used for suspension culture contains a bone morphogenetic protein signal transduction pathway activating substance and a substance acting on the Shh signal pathway. By the action of the bone morphogenetic protein signal transduction pathway activating substance and the substance acting on the Shh signal pathway, differentiation of hypothalamus neuroepithelial tissue and surface ectoderm from pluripotent stem cells is induced.

In the present invention, the bone morphogenetic factor signal transduction pathway activating substance is any substance that activates the pathway through which signals are transmitted upon binding of a bone morphogenetic factor and a receptor. Examples of the bone morphogenetic factor signal transduction pathway activating substance include BMP2, BMP4, BMP7, GDF5 and the like. Preferably, the bone morphogenetic factor signal transduction pathway activating substance is BMP4. While BMP4 is mainly described below, the bone morphogenetic factor signal transduction pathway activating substance to be used in the present invention is not limited to BMP4. BMP4 is a known cytokine, and the amino acid sequence thereof is also known. BMP4 to be used in the present invention is mammalian BMP4. Examples of the mammal include experiment animals such as rodents such as mouse, rat, hamster, guinea pig and the like, rabbit and the like; domestic animals such as swine, bovine, goat, horse, sheep and the like; companion animals such as dog, cat and the like; and primates such as human, monkey, orangutan, chimpanzee and the like. BMP4 is preferably BMP4 of rodents (mouse, rat etc.) or primates (human etc.), most preferably human BMP4. Human BMP4 means that BMP4 has the amino acid sequence of BMP4 naturally expressed in the human body. Examples of the representative amino acid sequence of human BMP4 include NCBI accession numbers NP_001193.2 (updated on Jun. 15, 2013), NP_570911.2 (updated on Jun. 15, 2013), NP_570912.2 (updated on Jun. 15, 2013), amino acid sequence obtained by removing the N-terminus signal sequence (1-24) from each of these amino acid sequences (mature form human BMP4 amino acid sequence) and the like.

In the present invention, the substance acting on the Shh signal pathway is not particularly limited as long as it can enhance signal transduction mediated by Shh. Examples of the substance acting on the Shh signal pathway include, but are not limited to, proteins belonging to the Hedgehog family (e.g., Shh), Shh receptor, Shh receptor agonist, Purmorphamine, Smoothened Agonist (SAG)(3-Chloro-N-[trans-4-(methylamino)cyclohexyl]-N-[[3-(4-pyridinyl)phenyl]methyl]-benzo[b]thiophene-2-carboxamide) and the like. Of these, SAG is preferable.

A preferable combination of a bone morphogenetic protein signal transduction pathway activating substance and a substance acting on the Shh signal pathway is that of BMP4 and SAG.

The concentration of the bone morphogenetic protein signal transduction pathway activating substance in the medium can be set as appropriate within a range permitting induction of differentiation of pluripotent stem cells into hypothalamus neuroepithelial tissue and surface ectoderm in the cell aggregate. When BMP4 is used as the bone morphogenetic protein signal transduction pathway activating substance, the concentration thereof is generally not less than 0.01 nM, preferably not less than 0.1 nM, more preferably not less than 1 nM. While the upper limit is not particularly set as long as no adverse effect on the differentiation into hypothalamus neuroepithelial tissue and surface ectoderm is found, it is generally not more than 1000 nM, preferably not more than 100 nM, more preferably not more than 10 nM from the aspects of culture costs. In one embodiment, the concentration of BMP4 in the medium is generally 0.01-1000 nM, preferably 0.1-100 nM, more preferably 1-10 nM (e.g., 5 nM). Since an exogenous bone morphogenetic protein signal transduction pathway activating substance particularly contributes to 1) aggressive formation of surface ectoderm, and 2) induction of differentiation of neuroepithelial tissue of hypothalamus rather than cerebrum in the cell aggregate, it is contained in the medium at a concentration capable of affording these effects.

It is not necessary for the bone morphogenetic protein signal transduction pathway activating substance to be contained in the medium over the entire period of the first culture step. For example, a bone morphogenetic protein signal transduction pathway activating substance may not be added to the medium for 2-4 days (e.g., 3 days) from the start of the suspension culture of pluripotent stem cell aggregates, and the bone morphogenetic protein signal transduction pathway activating substance may be added to the medium thereafter.

The concentration of the substance acting on the Shh signal pathway in the medium can be set as appropriate within a range permitting induction of differentiation of pluripotent stem cells into hypothalamus neuroepithelial tissue and surface ectoderm in the cell aggregate. When SAG is used as the substance acting on the Shh signal pathway, the concentration thereof is generally not less than 1 nM, preferably not less than 10 nM, more preferably not less than 100 nM. While the upper limit is not particularly set as long as no adverse effect on the differentiation into hypothalamus neuroepithelial tissue and surface ectoderm is found, it is generally not more than 1000 μM, preferably not more than 100 µM, more preferably not more than 10 µM from the aspects of culture costs. In one embodiment, the concentration of SAG in the medium is generally 1 nM-1000 µM, preferably 10 nM-100 µM, more preferably 100 nM-10 µM (e.g., 2 µM). Since an exogenous substance acting on the Shh signal pathway particularly plays a role of inducing differentiation of neuroepithelial tissue of hypothalamus (preferably ventral hypothalamus) rather than neural retina, it is contained in the medium at a concentration capable of affording this effect.

It is not necessary for the substance acting on the Shh signal pathway to be contained in the medium over the entire period of the first culture step. For example, a substance acting on the Shh signal pathway may not be added to the medium for 5-7 days (e.g., 6 days) from the start of the suspension culture of pluripotent stem cell aggregates, and a substance acting on the Shh signal pathway may be added to the medium thereafter.

In one embodiment, an aggregate of pluripotent stem cells is cultured in suspension for 2-4 days in a medium free of a bone morphogenetic protein signal transduction pathway activating substance and a substance acting on the Shh signal pathway, then the obtained aggregate is cultured in suspension for 2-4 days in a medium containing a bone morphogenetic protein signal transduction pathway activating substance and free of a substance acting on the Shh signal pathway, and further, the obtained aggregate is cultured in a medium containing a bone morphogenetic protein signal transduction pathway activating substance and a substance acting on the Shh signal pathway until a hypothalamus neuroepithelial tissue and surface ectoderm are induced.

The bone morphogenetic protein signal transduction pathway activating substance such as BMP4 and the like to be used in the present invention are preferably isolated. Being "isolated" means that an operation to remove factors other than the target component or cell has been performed, and the component or cell is no longer in a natural state. Therefore, "isolated protein X" does not include an endogenous protein X produced from the cell or tissue to be cultured. The purity of the "isolated protein X" (percentage of the weight of protein X to the total protein weight) is generally not less than 70%, preferably not less than 80%, more preferably not less than 90%, further preferably not less than 99%, most preferably 100%. The isolated bone morphogenetic protein signal transduction pathway activating substance contained in a medium used for suspension culture was exogenously added to the medium. Therefore, in one embodiment, the present invention comprises a step of exogenously adding an isolated bone morphogenetic protein signal transduction pathway activating substance to a medium to be used in the first culture step.

To suppress cell death of pluripotent stem cells (particularly, human pluripotent stem cells) induced by dispersion, it is preferable to add an inhibitor of Rho-associated coiled-coil kinase (ROCK) to a medium to be used in the first culture step from the start of cultivation (JP-A-2008-99662). A ROCK inhibitor is added for, for example, within 15 days, preferably within 10 days, more preferably within 6 days, from the start of the culture. Examples of the ROCK inhibitor include Y-27632 ((+)-(R)-trans-4-(1-aminoethyl)-N-(4-pyridyl)cyclohexanecarboxamide dihydrochloride) and the like. The concentration of the ROCK inhibitor used for suspension culture is a concentration capable of suppressing cell death of pluripotent stem cells induced by dispersion. For example, for Y-27632, this concentration is normally about 0.1 to 200 µM, preferably about 2 to 50 µM.

The concentration of the ROCK inhibitor may be changed in the addition period thereof and, for example, the concentration may be reduced to half in the latter half period.

The medium to be used for suspension culture of cell aggregate can be prepared using a medium used for culturing mammalian cells as a basal medium. The basal medium is not particularly limited as long as it can be used for culture of mammalian cells and may be BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, Ham's F-12 medium, RPMI 1640 medium, Fischer's medium, Neurobasal medium, a mixed medium thereof and the like. In one embodiment, a mixed medium of IMDM medium and Ham's F-12 medium is used. The mixing ratio is, for example, IMDM:Ham's F-12=0.8-1.2:1.2-0.8, in a volume ratio.

The medium to be used for culture may be a serum-containing medium or serum-free medium. To avoid contamination with chemically-undefined components, the medium used for culturing cell aggregates in suspension is preferably a serum-free medium.

The medium used for suspension culture of cell aggregates may contain a serum alternative. The serum alternative may, for example, be one comprising as appropriate albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of a method of the present invention, commercially available serum alternatives can be utilized. Examples of such commercially available serum alternatives include KSR (Knockout Serum Replacement) (produced by Invitrogen), Chemically-defined Lipid Concentrated (produced by Gibco Company) and Glutamax (produced by Gibco Company).

The medium used for culturing the cell aggregate in suspension can contain other additive as long as an adverse influence is not exerted on the induction of differentiation of pluripotent stem cells into hypothalamus neuroepithelial tissue and surface ectoderm. Examples of the additive include, but are not limited to, insulin, iron source (e.g., transferrin etc.), minerals (e.g., sodium selenate etc.), saccharides (e.g., glucose etc.), organic acids (e.g., pyruvic acid, lactic acid etc.), serum proteins (e.g., albumin etc.), amino acids (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

In one embodiment, to avoid an adverse influence on the induction of differentiation into a hypothalamus neuroepithelial tissue and surface ectoderm, the medium used for suspension culture of cell aggregates is a chemically synthesized medium free of a growth factor other than those particularly described in the present specification to be contained in a medium (growth-factor-free Chemically Defined Medium; gfCDM), which is supplemented with a serum replacement (KSR etc.). The "growth factor" here encompasses a pattern formation factor such as Fgf; BMP; Wnt, Nodal, Notch, Shh and the like; insulin and Lipid-rich albumin. Examples of the chemically synthesized medium free of a growth factor include gfCDM disclosed in Wataya et al, Proc Natl Acad Sci USA, 105(33): 11796-11801, 2008.

Other culture conditions of the suspension culture of cell aggregate such as culture temperature, $CO_2$ concentration, $O_2$ concentration and the like can be appropriately set. The culture temperature is, for example, about 30-40° C., preferably about 37° C. The $CO_2$ concentration is, for example, about 1-10%, preferably about 5%. The $O_2$ concentration is, for example, about 20%.

In a preferable embodiment, a qualitatively uniform population of aggregates of pluripotent stem cells is cultured in suspension in a medium containing a bone morphogenetic protein signal transduction pathway activating substance and substance acting on the Shh signal pathway. Using a qualitatively uniform population of aggregates of pluripotent stem cells, difference in levels of differentiation into adenohypophysis or a precursor tissue thereof between aggregates can be suppressed to the minimum, and the efficiency of the intended differentiation induction can be improved. Suspension culture of a qualitatively uniform population of aggregates of pluripotent stem cells encompasses the following embodiments.

(1) Plural culture compartments are prepared, and a qualitatively uniform population of aggregates of pluripotent stem cells is seeded such that one pluripotent stem cell aggregate is contained in one culture compartment (e.g., one pluripotent stem cell aggregate is placed in each well of 96 well plate). In each culture compartment, one pluripotent stem cell aggregate is cultured in suspension in a medium containing a bone morphogenetic protein signal transduction pathway activating substance and a substance acting on the Shh signal pathway.

(2) A qualitatively uniform population of aggregates of pluripotent stem cells is seeded such that plural aggregates of pluripotent stem cells are contained in one culture compartment (e.g., plural aggregates of pluripotent stem cells are placed in a 10 cm dish). In the culture compartment, plural aggregates of pluripotent stem cells are cultured in suspension in a medium containing a bone morphogenetic protein signal transduction pathway activating substance and a substance acting on the Shh signal pathway.

Any of the embodiments (1) and (2) may be employed for the method of the present invention and the embodiment may be changed during culture (from embodiment (1) to embodiment (2), or from embodiment (2) to embodiment (1)). In one embodiment, the embodiment of (1) is employed in the first culture step and the embodiment of (2) is employed in the second culture step.

The first culture step is performed for a period sufficient for inducing differentiation of a hypothalamus neuroepithelial tissue and surface ectoderm from pluripotent stem cells. Differentiation into a hypothalamus neuroepithelial tissue and surface ectoderm can be detected by, for example, RT-PCR or immunohistochemistry using an antibody specific to a marker of hypothalamus neuroepithelial tissue or surface ectoderm. For example, the first culture step is performed until not less than 10%, preferably not less than 30%, more preferably not less than 50%, of cell aggregates in the culture contains a hypothalamus neuroepithelial tissue and surface ectoderm. While the culture period cannot be unconditionally specified since it can vary depending on the animal species of the pluripotent stem cell, and the kind of the bone morphogenetic protein signal transduction pathway activating substance and the substance acting on the Shh signal pathway, the first culture step is, for example, generally 15-20 days (e.g., 18 days) when a human pluripotent stem cell is used.

By performing the first culture step, a cell aggregate containing a hypothalamus neuroepithelial tissue and surface ectoderm can be obtained.

The hypothalamus neuroepithelial tissue is a neuroepithelial tissue expressing a hypothalamus marker. The hypothalamus includes ventral hypothalamus and dorsal hypothalamus. As a hypothalamus marker, NKx2.1 (ventral hypothalamus marker), Pax6 (dorsal hypothalamus marker) and the like can be mentioned. In one embodiment, the ventral hypothalamus neuroepithelial tissue is an Rx-positive, Chx10-negative, and Nkx2.1-positive neuroepithelial tissue. In one embodiment, the dorsal hypothalamus neuroepithelial tissue is an Rx-positive, Chx10-negative, and Pax6-positive neuroepithelial tissue. The hypothalamus neuroepithelial tissue contained in the obtained cell aggregate in the first culture step is preferably a ventral hypothalamus neuroepithelial tissue.

The surface ectoderm is an ectodermal cell layer formed on the surface layer of the embryo in the embryogenic development. As the surface ectoderm marker, pan-cytokeratin can be mentioned. Surface ectoderm can generally differentiate into hypophysis anterior, skin, mouth cavity epithelium, dental enamel, dermal gland and the like. In one embodiment, the surface ectoderm is an E-cadherin-positive and pan-cytokeratin-positive cell layer.

Preferably, hypothalamus neuroepithelial tissues occupy the inside of the cell aggregate obtained in the first culture step, and the cells of a single layer surface ectoderm constitutes the surface of the cell aggregate. The surface ectoderm may contain thickened epidermal placode in a part thereof.

(3.2) Second Culture Step

In the second culture step, the cell aggregate containing a hypothalamus neuroepithelial tissue and surface ectoderm, which is obtained in the first culture step, is further cultured in suspension in a medium containing a bone morphogenetic protein signal transduction pathway activating substance and a substance acting on the Shh signal pathway, whereby a cell aggregate containing 1) a hypothalamus neuroepithelial tissue, and 2) hypophysial placode and/or Rathke's pouch is obtained. By the action of the bone morphogenetic protein signal transduction pathway activating substance and the substance acting on the Shh signal pathway, further differentiation of surface ectoderm into hypophysial placode and/or Rathke's pouch is induced.

The definitions of the bone morphogenetic protein signal transduction pathway activating substance and the substance acting on the Shh signal pathway are as described in the explanation of the first culture step.

Preferably, the bone morphogenetic protein signal transduction pathway activating substance to be used in the second culture step is BMP4 as in the first culture step. Preferably, the substance acting on the Shh signal pathway to be used in the second culture step is SAG as in the first culture step.

A preferable combination of the bone morphogenetic protein signal transduction pathway activating substance and the substance acting on the Shh signal pathway is that of BMP4 and SAG.

The concentration of the bone morphogenetic factor signal transduction pathway activating substance in the medium can be appropriately determined within a range in which differentiation of surface ectoderm into hypophysial placode and/or Rathke's pouch can be induced in the cell aggregate. When BMP4 is used as a bone morphogenetic factor signal transduction pathway activating substance, the concentration thereof is generally not less than 0.01 nM, preferably, not less than 0.1 nM, more preferably not less than 1 nM. While the upper limit is not particularly set as long as no adverse effect on the differentiation of surface ectoderm into hypophysial placode and/or Rathke's pouch is found, it is generally not more than 1000 nM, preferably not more than 100 nM, more preferably not more than 10 nM from the aspects of culture costs. In one embodiment, the concentration of BMP4 in the medium is generally 0.01-1000 nM, preferably 0.1-100 nM, more preferably 1-10 nM (e.g., 5 nM). The concentration of the bone morphogenetic protein signal transduction pathway activating substance may be varied within the addition period. For example, the concentration may be set at the aforementioned concentration at the time of the start of the second culture step, and may be decreased to half every 2-4 days.

The concentration of the substance acting on the Shh signal pathway in the medium can be set as appropriate within a range permitting induction of differentiation of surface ectoderm into hypophysial placode or Rathke's pouch in the cell aggregate. When SAG is used as the substance acting on the Shh signal pathway, the concentration thereof is generally not less than 1 nM, preferably not less than 10 nM, more preferably not less than 100 nM. While the upper limit is not particularly set as long as no adverse effect on the differentiation into hypophysial placode or Rathke's pouch is found, it is generally not more than 1000 μM, preferably not more than 100 μM, more preferably not more than 10 μM from the aspects of culture costs. In one embodiment, the concentration of SAG in the medium is generally 1 nM-1000 μM, preferably 10 nM-100 μM, more preferably 100 nM-10 μM (e.g., 2 μM).

In a preferable embodiment, the medium to be used in the second culture step contains FGF2. FGF2 promotes differentiation of surface ectoderm into hypophysial placode.

FGF2 is a known cytokine also called basic fibroblast growth factor (bFGF), and its amino acid sequence is also known. FGF2 to be used in the present invention is generally mammalian FGF2. Examples of the mammal include those mentioned above. Since FGF2 has cross-reactivity among many mammalian species, FGF2 of any mammal may also be used as long as the object of the present invention can be achieved. Preferably, a mammalian FGF2 of the same species as the cell to be cultured is used. For example, FGF2 of rodents (mouse, rat etc.) or primates (human etc.) is used. Here, mouse FGF2 means that FGF2 has the amino acid sequence of FGF2 naturally expressed in the body of mouse. In the present specification, similar interpretation is also applied to other proteins and the like. Examples of the representative amino acid sequence of mouse FGF2 include NCBI accession No. NP_032032.1 (updated Feb. 18, 2014), an amino acid sequence obtained by removing the N-terminal signal sequence (1-9) from said amino acid sequence (mature mouse FGF2 amino acid sequence) and the like. Examples of the representative amino acid sequence of human FGF2 include NCBI accession No. NP_001997.5 (updated Feb. 18, 2014) and the like.

While the concentration of FGF2 in the medium is not particularly limited as long as it can promote differentiation of surface ectoderm into hypophysial placode, it is generally not less than 1 ng/ml, preferably not less than 10 ng/ml. While the upper limit of FGF2 concentration is not particularly set as long as no adverse effect on the differentiation into hypophysial placode and/or Rathke's pouch is found, it is generally not more than 1000 ng/ml, preferably not more than 500 ng/ml, from the aspects of culture costs. In one embodiment, the concentration of FGF2 in the medium is generally 1-1000 ng/ml, preferably 10-100 ng/ml.

The bone morphogenetic protein signal transduction pathway activating substance such as BMP4 and the like and FGF2 to be used in the present invention are preferably isolated. The isolated bone morphogenetic protein signal transduction pathway activating substance and isolated FGF2 contained in a medium used in the second culture step were exogenously added to the medium. Therefore, in one embodiment, the present invention comprises a step of exogenously adding an isolated bone morphogenetic protein signal transduction pathway activating substance (and optionally, isolated FGF2) to a medium to be used in the second culture step.

The medium to be used for the second culture step can be prepared by using a medium used for culturing mammalian cells as a basal medium, as in the medium used in the first culture step. The basal medium is not particularly limited as long as it can be used for culture of mammalian cells and may be BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, Ham's F-12 medium, RPMI 1640 medium, Fischer's medium, Neurobasal medium, a mixed medium thereof and the like. In one embodiment, a mixed medium of IMDM medium and Ham's F-12 medium is used. The mixing ratio is, for example, IMDM:Ham's F-12=0.8-1.2: 1.2-0.8, in a volume ratio.

The medium to be used for culture may be a serum-containing medium or serum-free medium. To avoid contamination with chemically-undefined components, the medium used for culturing cell aggregates in suspension is preferably a serum-free medium.

The medium used for suspension culture of cell aggregates may contain a serum alternative. The serum alternative may, for example, be one comprising as appropriate an albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of a method of the present invention, commercially available serum alternatives can be utilized. Examples of such commercially available serum alternatives include KSR (Knockout Serum Replacement) (produced by Invitrogen), Chemically-defined Lipid Concentrated (produced by Gibco Company) and Glutamax (produced by Gibco Company).

The medium used for culturing the cell aggregate in suspension can contain other additive as long as an adverse influence is not exerted on the induction of differentiation of surface ectoderm into hypophysial placode and/or Rathke's pouch. Examples of the additive include, but are not limited to, insulin, iron source (e.g., transferrin etc.), minerals (e.g., sodium selenate etc.), saccharides (e.g., glucose etc.), organic acids (e.g., pyruvic acid, lactic acid etc.), serum proteins (e.g., albumin etc.), amino acids (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

In one embodiment, to avoid an adverse influence on the induction of differentiation into hypophysial placode and/or Rathke's pouch, the medium used for suspension culture of cell aggregates is a chemically synthesized medium free of a growth factor other than those particularly described in the present specification to be contained in a medium (growth-factor-free Chemically Defined Medium; gfCDM), which is supplemented with a serum replacement (KSR etc.). The "growth factor" here encompasses a pattern formation factor such as Fgf; BMP; Wnt, Nodal, Notch, Shh and the like; insulin and Lipid-rich albumin. Examples of the chemically synthesized medium free of a growth factor include gfCDM disclosed in Wataya et al, Proc Natl Acad Sci USA, 105(33): 11796-11801, 2008.

The suspension culture in the second culture step is preferably performed under high oxygen partial pressure conditions. When a cell aggregate containing hypothalamus neuroepithelial tissue and surface ectoderm is further cultured in suspension under high oxygen partial pressure conditions, delivery of oxygen to the inside of the cell aggregate, and maintenance culture of the cell aggregate for a long period are achieved, which enables efficient induction of differentiation into hypophysial placode and/or Rathke's pouch.

The high oxygen partial pressure condition means an oxygen partial pressure condition exceeding the oxygen partial pressure in the air (20%). The oxygen partial pressure in the second culture step is, for example, 30-60%, preferably 35-60%, more preferably 38-60%.

Other culturing conditions such as culturing temperature and $CO_2$ concentration in the second culture step can be set as appropriate. The culturing temperature is, for example, about 30 to 40° C., preferably about 37° C. The $CO_2$ concentration is, for example, about 1 to 10%, preferably about 5%.

The second culture step is performed for a period sufficient for inducing differentiation of surface ectoderm into hypophysial placode and/or Rathke's pouch. By performing the second culture step, hypophysial placode is formed in the surface ectoderm. Some or all of the hypophysial placodes may invaginate into the inside of the cell aggregate (i.e., adjacent hypothalamus neuroepithelium) to form Rathke's pouch. Differentiation of surface ectoderm into hypophysial placode and/or Rathke's pouch essentially requires interaction between the surface ectoderm and hypothalamus neuroepithelial tissue (preferably, ventral hypothalamus neuroepithelial tissue). In the present invention, by the first culture step, hypothalamus neuroepithelial tissue and surface ectoderm are simultaneously formed in the cell aggregate; in a preferable embodiment, hypothalamus neuroepithelial tissue occupies the inside of the cell aggregate and the cells of a single layer surface ectoderm constitute the surface of the cell aggregate. As a result, good interaction between the adjacent surface ectoderm and hypothalamus neuroepithelial tissue becomes possible within the cell aggregates, and the process of self-organization of the hypophysis in the embryogenic development such as hypophysial placode formation in surface ectoderm, invagination of hypophysial placode, formation of Rathke's pouch and the like can be reproduced in vitro. Differentiation into hypophysial placode and/or Rathke's pouch can be confirmed by, for example, detecting the formation of hypophysis progenitor cell marker-positive placode or sac structure by immunohistochemistry using specific antibodies against hypophysis progenitor cell marker (e.g., Lim3, Pitx1, Isl1/2 etc.). For example, the second culture step is performed until not less than 10%, preferably not less than 30%, more preferably not less than 50%, of cell aggregates in the culture contains hypophysial placode and/or Rathke's pouch. While the culture period cannot be unconditionally specified since it can vary depending on the animal species of the pluripotent stem cell, and the kind of the bone morphogenetic protein signal transduction pathway activating substance and the substance acting on the Shh signal pathway, the second culture step is, for example, generally not less than 6 days, for example, 6-12 days, when a human pluripotent stem cell is used.

By performing the second culture step, a cell aggregate comprising 1) hypothalamus neuroepithelial tissue, and 2) hypophysial placode and/or Rathke's pouch can be obtained.

(3.3) Third Culture Step

The cell aggregate comprising 1) hypothalamus neuroepithelial tissue, and 2) hypophysial placode and/or Rathke's pouch, which is obtained in the second culture step, is further cultured in suspension in a medium containing a substance acting on the Shh signal pathway, whereby a cell aggregate containing adenohypophysis can be obtained (third culture step). By the third culture step, differentiation of hypophysial placode and/or Rathke's pouch into pituitary hormone-producing cells is induced, and pituitary hormone-producing cells are produced in the hypophysial placode and/or Rathke's pouch, whereby adenohypophysis can be formed.

The definition of the substance acting on the Shh signal pathway is as described in the explanation of the first culture step.

Preferably, the substance acting on the Shh signal pathway to be used in the third culture step is SAG as in the first and the second culture steps.

The concentration of the substance acting on the Shh signal pathway in the medium can be set as appropriate within a range permitting induction of differentiation of hypophysial placode and/or Rathke's pouch into pituitary hormone-producing cells in the cell aggregate. When SAG is used as the substance acting on the Shh signal pathway, the concentration thereof is generally not less than 1 nM, preferably not less than 10 nM, more preferably not less than 100 nM. While the upper limit is not particularly set as long as no adverse effect on the differentiation into pituitary hormone-producing cells is found, it is generally not more than 1000 µM, preferably not more than 100 µM, more preferably not more than 10 µM from the aspects of culture costs. In one embodiment, the concentration of SAG in the medium is generally 1 nM-1000 µM, preferably 10 nM-100 µM, more preferably 100 nM-10 µM (e.g., 2 µM).

In a preferable embodiment, the medium to be used in the third culture step contains FGF2. FGF2 promotes differentiation of hypophysial placode and/or Rathke's pouch into pituitary hormone-producing cells.

The definition of FGF2 is as described in the explanation of the second culture step.

While the concentration of FGF2 in the medium is not particularly limited as long as it can promote differentiation of hypophysial placode and/or Rathke's pouch into pituitary hormone-producing cells, it is generally not less than 1 ng/ml, preferably not less than 10 ng/ml. While the upper limit of FGF2 concentration is not particularly set as long as no adverse effect on the differentiation into pituitary hormone-producing cells is found, it is generally not more than 1000 ng/ml, preferably not more than 500 ng/ml, from the aspects of culture costs. In one embodiment, the concentration of FGF2 in the medium is generally 1-1000 ng/ml, preferably 10-100 ng/ml.

In a preferable embodiment, the medium to be used in the third culture step contains a Notch signal inhibitor. The Notch signal inhibitor promotes differentiation of hypophysial placode and/or Rathke's pouch into pituitary hormone-producing cells (particularly, ACTH-producing cells). The Notch signal inhibitor increases the expression of the transcription factor Tbx19 that performs upstream regulation of ACTH production.

The Notch signal inhibitor is not particularly limited as long as it can suppress signal transduction mediated by Notch. Examples of the Notch signal inhibitor include gamma secretase inhibitors such as DAPT (N—[N-(3,5-difluorophenacetyl)-l-alanyl]-S-phenylglycine t-butyl ester), DBZ, MDL28170 and the like. Of these, DAPT is preferable.

While the concentration of Notch signal inhibitor in the medium is not particularly limited as long as it can promote differentiation of hypophysial placode and/or Rathke's pouch into pituitary hormone-producing cells (particularly, ACTH-producing cells), in the case of DAPT, for example, it is generally not less than 0.1 µM, preferably not less than 1 µM. While the upper limit of DAPT concentration is not particularly set as long as no adverse effect on the differentiation into pituitary hormone-producing cells is found, it is generally not more than 1000 µM, preferably not more than 100 µM, from the aspects of culture costs. In one embodiment, the DAPT concentration of the medium is generally 0.1-1000 µM, preferably 1-100 µM (e.g., 10 µM).

In the third culture step, addition of a bone morphogenetic protein signal transduction pathway activating substance to the medium is not necessary. In one embodiment, the medium to be used in the third culture step does not contain a bone morphogenetic protein signal transduction pathway activating substance.

FGF2 to be used in the present invention are preferably isolated. The isolated FGF2 contained in a medium used in the third culture step were exogenously added to the medium. Therefore, in one embodiment, the present invention includes a step of exogenously adding isolated FGF2 to a medium to be used in the third culture step.

In the third culture step, cell aggregates may be treated with corticosteroids by the addition of corticosteroids to the medium. By the corticosteroids treatment, differentiation of hypophysial placode and/or Rathke's pouch into pituitary hormone-producing cells other than ACTH-producing cells (i.e., GH-producing cells, PRL-producing cells, TSH-producing cells, LH-producing cells, FSH-producing cells etc.) is promoted. Examples of the corticosteroids include, but are not limited to, natural glucocorticoids such as hydrocortisone, cortisone acetate, fludrocortisone acetate and the like; and artificially synthesized glucocorticoids such as dexamethasone, betamethasone, predonisolone, methylprednisolone, and triamcinolone and the like.

The concentration of corticosteroids in the medium is not particularly limited as long as it can promote differentiation of hypophysial placode and/or Rathke's pouch into pituitary hormone-producing cells (excluding ACTH-producing cells) and can be appropriately determined according to the kind of corticosteroids. In the case of hydrocortisone, for example, it is generally not less than 100 ng/ml, preferably not less than 1 µg/ml. While the upper limit of hydrocortisone concentration is not particularly set as long as no adverse effect on the differentiation into pituitary hormone-producing cells (excluding ACTH-producing cells) is found, it is generally not more than 1000 µg/ml, preferably not more than 100 µg/ml, from the aspects of culture costs. In one embodiment, the concentration of hydrocortisone in the medium is generally 100 ng/ml-1000 µg/ml, preferably 1-100 µg/ml. When dexamethasone is used as the corticosteroids, the concentration thereof in the medium can be set to about 1/25 of hydrocortisone.

In the third culture step, the timing for adding corticosteroids to the medium is not particularly limited as long as differentiation of hypophysial placode and/or Rathke's pouch into pituitary hormone-producing cells (excluding ACTH-producing cells) can be promoted, and corticosteroids may be added to the medium from the start of the third culture step, or added to the medium after culture for a given period in a medium free of corticosteroids after the start of the third culture step. Preferably, corticosteroids are added to the medium at a stage when emergence of ACTH-producing cells is confirmed in the cell aggregate after the start of the third culture step. That is, cell aggregates are cultured in a medium free of corticosteroids until the emergence of ACTH-producing cells is confirmed in the cell aggregate, and after confirmation of the emergence of ACTH-producing cells, the third culture step is continued in a medium containing corticosteroids. The emergence of ACTH-producing cells can be confirmed by immunohistochemical staining using an antibody against ACTH. When a human pluripotent stem cell is used, emergence of ACTH-producing cell can be generally expected on day 37 or thereafter from the start of the third culture step. In one embodiment, therefore, corticosteroids are added to the medium on day 37 or thereafter from the start of the third culture step.

While the period of treatment of cell aggregate with corticosteroids is not particularly limited as long as differentiation of hypophysial placode and/or Rathke's pouch into pituitary hormone-producing cells (excluding ACTH-producing cells) can be promoted, generally, cell aggregates are treated with corticosteroids until promotion of differentiation into pituitary hormone-producing cells (excluding ACTH-producing cells) is confirmed in a corticosteroid-treated group as compared to a corticosteroids non-treated group. The treatment period is generally not less than 7 days, preferably not less than 12 days. While the upper limit of the treatment period is not particularly set, the corticosteroids may be removed from the medium at a stage when promotion of differentiation into pituitary hormone-producing cells (excluding ACTH-producing cells) is confirmed in a corticosteroid-treated group as compared to a corticosteroids non-treated group.

The addition of corticosteroids to the medium acts suppressively on the differentiation induction of ACTH-producing cells due to feedback inhibition.

The medium to be used in the third culture step can be prepared using a medium used for culturing mammalian cells as a basal medium, as for the medium used for the first and second culture steps. The basal medium is not particularly limited as long as it can be used for culture of mammalian cells and may be BME medium, BGJb medium, CMRL 1066 medium, Glasgow MEM medium, Improved MEM Zinc Option medium, IMDM medium, Medium 199 medium, Eagle MEM medium, aMEM medium, DMEM medium, ham medium, Ham's F-12 medium, RPMI 1640 medium, Fischer's medium, Neurobasal medium, a mixed medium thereof and the like. In one embodiment, a mixed medium of IMDM medium and Ham's F-12 medium is used. The mixing ratio is, for example, IMDM:Ham's F-12=0.8-1.2:1.2-0.8, in a volume ratio.

The medium to be used for culture may be a serum-containing medium or a serum-free medium. To avoid contamination with chemically-undefined components, a serum-free medium is preferably used for suspension culture of cell aggregates.

The medium used for suspension culture of cell aggregates may contain a serum alternative. The serum alternative may, for example, be one comprising as appropriate albumin, transferrin, fatty acids, collagen precursor, trace elements, 2-mercaptoethanol or 3'-thiolglycerol, or their equivalents and the like. Such a serum alternative can be prepared by, for example, a method described in WO98/30679. To facilitate easier implementation of a method of the present invention, commercially available serum alternatives can be utilized. Examples of such commercially available serum alternatives include KSR (Knockout Serum Replacement) (produced by Invitrogen), Chemically-defined Lipid Concentrated (produced by Gibco Company) and Glutamax (produced by Gibco Company).

The medium used for suspension culture of cell aggregates can contain other additive as long as induction of differentiation of pluripotent stem cells into hypophysial placode and/or of Rathke's pouch into pituitary hormone-producing cells is not adversely influenced. Examples of the additive include, but are not limited to, insulin, iron source (e.g., transferrin etc.), minerals (e.g., sodium selenate etc.), saccharides (e.g., glucose etc.), organic acids (e.g., pyruvic acid, lactic acid etc.), serum proteins (e.g., albumin etc.), amino acids (e.g., L-glutamine etc.), reducing agent (e.g., 2-mercaptoethanol etc.), vitamins (e.g., ascorbic acid, d-biotin etc.), antibiotic (e.g., streptomycin, penicillin, gentamicin etc.), buffering agent (e.g., HEPES etc.) and the like.

In one embodiment, to avoid an adverse influence on the induction of differentiation into pituitary hormone-producing cells, the medium used for suspension culture of cell aggregates is a chemically synthesized medium free of a growth factor other than those particularly described in the present specification to be contained in a medium (growth-factor-free Chemically Defined Medium; gfCDM), which is supplemented with a serum replacement (KSR etc.). The "growth factor" here encompasses a pattern formation factor such as Fgf; BMP; Wnt, Nodal, Notch, Shh and the like; insulin and Lipid-rich albumin. Examples of the chemically synthesized medium free of a growth factor include gfCDM disclosed in Wataya et al, Proc Natl Acad Sci USA, 105(33): 11796-11801, 2008.

The suspension culture in the third culture step is preferably performed under a high oxygen partial pressure condition. When a cell aggregate containing 1) hypothalamus neuroepithelial tissue, and 2) hypophysial placode and/or Rathke's pouch is further cultured in suspension under high oxygen partial pressure conditions, delivery of oxygen to the inside of the cell aggregate, and maintenance culture of the cell aggregate for a long period are achieved, which enables efficient induction of differentiation into pituitary hormone-producing cells.

The high oxygen partial pressure condition means an oxygen partial pressure condition exceeding the oxygen partial pressure in the air (20%). The oxygen partial pressure in the third culture step is, for example, 30-60%, preferably 35-60%, more preferably 38-60%.

Other culturing conditions in the third culture step, such as culturing temperature, $CO_2$ concentration and the like, can be set as appropriate. The culturing temperature is not particularly limited, and is, for example, about 30 to 40° C., preferably about 37° C. The $CO_2$ concentration is, for example, about 1 to 10%, preferably about 5%.

The third culture step is performed for a period sufficient for inducing differentiation of hypophysial placode and/or Rathke's pouch into pituitary hormone-producing cells. By performing the third culture step, differentiation of hypophysial placode and/or Rathke's pouch into pituitary hormone-producing cells is induced, and pituitary hormone-producing cells are produced in the hypophysial placode and/or Rathke's pouch, whereby adenohypophysis can be formed. Examples of the pituitary hormone-producing cells induced from hypophysial placode and/or Rathke's pouch include growth hormone (GH)-producing cells, prolactin (PRL)-producing cells, adrenocorticotropic hormone (ACTH)-producing cells. In a preferable embodiment, the adrenocorticotropic hormone (ACTH)-producing cells secrete ACTH in response to CRH stimulation, and the ACTH secretion is suppressed in a feedback manner by glucocorticoids. In one embodiment, differentiation of hypophysial placode and/or Rathke's pouch into at least one kind, preferably two kinds, more preferably three kinds, of pituitary hormone-producing cells selected from the group consisting of growth hormone (GH)-producing cells, prolactin (PRL)-producing cells, and adrenocorticotropic hormone (ACTH)-producing cells is induced, and adenohypophysis containing at least one kind, preferably two kinds, more preferably three kinds, of pituitary hormone-producing cells selected from the group consisting of growth hormone (GH)-producing cells, prolactin (PRL)-producing cells, and adrenocorticotropic hormone (ACTH)-producing cells is formed. Other pituitary hormone-producing cells such as thyroid-stimulating hormone (TSH)-producing cells, follicle-stimulating hormone (FSH)-producing cells, luteinizing hormone (LH)-producing cells, melanocyte-stimulating hormone (MSH)-producing cells and the like may be induced from hypophysial placode and/or Rathke's pouch, besides growth hormone (GH)-producing cells, prolactin (PRL)-producing cells, and adrenocorticotropic hormone (ACTH)-producing cells. That is, adenohypophysis formed by the third culture step may comprise other pituitary hormone-producing cells such as thyroid-stimulating hormone (TSH)-producing cells, follicle-stimulating hormone (FSH)-producing cells, luteinizing hormone (LH)-producing cells, melanocyte-stimulating hormone (MSH)-producing cells and the like, in addition to at least one kind, preferably two kinds, more preferably three kinds, selected from the group consisting of growth hormone (GH)-producing cells, prolactin (PRL)-producing cells, and adrenocorticotropic hormone (ACTH)-producing cells. Differentiation into pituitary hormone-producing cells can be confirmed by, for example, detecting the pituitary hormone positive cell by immunohistochemistry using specific antibodies against pituitary hormone. For example, the third culture step is performed until not less than 10%, preferably not less than 30%, more preferably not less than 50%, of cell aggregates in the culture contains pituitary hormone-producing cells. While the culture period cannot be unconditionally specified since it can vary depending on the animal species of the pluripotent stem cell, and the kind of the substance acting on the Shh signal pathway, the third culture step is performed, for example, for generally not less than 37 days (e.g., 37-70 days) when a human pluripotent stem cell is used.

By performing the third culture step, a cell aggregate comprising adenohypophysis can be obtained.

Suspension culture of the cell aggregate may be performed in the presence or absence of feeder cells as long as the differentiation induction from pluripotent stem cells into adenohypophysis or a precursor tissue thereof is possible by the production method of the present invention. To avoid contamination with undefined factors, the suspension culture of aggregate is preferably performed in the absence of feeder cells.

In the production method of the present invention, a culture vessel to be used for suspension-culture of cell aggregates is not particularly limited. Such culture vessel includes, for example, flasks, tissue culture flasks, dishes, Petri dishes, tissue culture dishes, multi-dishes, microplates, micro-well plates, micropores, multi-plates, multi-well plates, chamber slides, bowls, tubes, trays, culture bags, and roller bottles. To enable culture under non-adhesive conditions, the culture vessel is preferably non-cell-adherent. Useful non-cell-adherent culture vessels include culture vessels whose surfaces have been artificially treated to be non-cell-adherent, culture vessels whose surfaces have not undergone an artificial treatment for improving the cell adhesiveness (e.g., coating treatment with an extracellular matrix and the like), and the like.

As a culture vessel to be used for suspension culture of cell aggregates, an oxygen-permeable one may be used. Using an oxygen-permeable culture vessel, oxygen supply to the cell aggregates may be improved, thus contributing to the maintenance culture of the cell aggregates for a long term.

In the suspension culture of aggregate, the aggregate may be subjected to static culture or may be intentionally moved by rotation culture or shaking culture, as long as a non-adhered state of the aggregate to the culture vessel can be maintained. However, it is not necessary to intentionally move aggregates by rotation culture or shaking culture in the present invention. In one embodiment, the suspension culture in the production method of the present invention is performed by static culture. Static culture refers to a culture method for cultivating aggregate in a state free of intentional movement of the aggregate. It may happen that aggregate move, for example, due to the convection of the medium along with topical changes in the medium temperature. However, since the aggregate are not intentionally moved, such case is also included in the static culture in the present invention. Static culture may be performed during the whole period of suspension culture, or only during a part of the period. In a preferable embodiment, static culture may be performed during the whole period of suspension culture. Static culture requires no apparatus and is expected to cause less damage on the cell aggregate, and is advantageous since the amount of the culture medium can be small.

(4) Use of Cell Aggregate, Isolated Adenohypophysis or Precursor Tissue Thereof, and Pituitary Hormone-Producing Cells In a further aspect, adenohypophysis or a precursor tissue thereof (hypophysial placode, Rathke's pouch etc.) can be isolated from the cell aggregate obtained as mentioned above. Also, by treating adenohypophysis with protease such as trypsin and the like and/or EDTA etc., pituitary hormone-producing cells can be isolated. The present invention provides the cell aggregate, adenohypophysis or precursor tissue thereof, and pituitary hormone-producing cells obtainable by the above-mentioned method of the present invention.

The cell aggregate, adenohypophysis or precursor tissue thereof, and pituitary hormone-producing cells obtained by the method of the present invention can be used for transplantation therapy. For example, as a therapeutic drug for a disease resulting from a disorder of adenohypophysis (anterior or intermediate, preferably anterior), or for supplementing a relevant damaged part in the damaged condition of adenohypophysis (anterior or intermediate, preferably anterior), the cell aggregate, adenohypophysis or precursor tissue thereof, or pituitary hormone-producing cells obtained by the method of the present invention can be used. By transplanting the cell aggregate, adenohypophysis or precursor tissue thereof, or pituitary hormone-producing cells obtained by the present invention to a patient with a disease resulting from a disorder of adenohypophysis, or a damaged condition of adenohypophysis, the disease resulting from a disorder of adenohypophysis, or the damaged condition of adenohypophysis can be treated. The transplantation site is not particularly limited as long as the transplanted cell aggregate, adenohypophysis or precursor tissue thereof, and pituitary hormone-producing cells can function as an alternative to the disordered adenohypophysis and, for example, under the kidney capsule and the like can be mentioned.

Examples of the disease resulting from a disorder of adenohypophysis include panhypopituitarism, pituitary dwarfism, adrenocortical insufficiency, partial hypopituitarism, isolated deficiency of anterior pituitary hormone and the like. Furthermore, examples of these damaged condition of the adenohypophysis include adenohypophysectomied patients, patients after radiation on hypophysis tumor, trauma.

In transplantation therapy, rejection due to the difference in histocompatibility antigens often poses a problem. However, the problem can be solved by using pluripotent stem cells (e.g., induced pluripotent stem cells) established from the somatic cell of the transplantation recipient. That is, in a preferable embodiment, pluripotent stem cells (e.g., induced pluripotent stem cells) established from the somatic cell of the recipient are used as pluripotent stem cells in the method of the present invention, and adenohypophysis or a precursor tissue thereof, or a pituitary hormone-producing cells, which is immunologically self for the recipient, are produced and transplanted to the recipient.

Furthermore, cell aggregate, adenohypophysis or a precursor tissue thereof, or pituitary hormone-producing cells, which are obtained by the present invention, can be used for screening and evaluation of drugs. Particularly, since adenohypophysis or a precursor tissue thereof, obtainable by the present invention, has a higher structure similar to that of adenohypophysis or a precursor tissue thereof in the body, it can be applied to screening for a therapeutic drug for diseases resulting from disorders of adenohypophysis, and damaged adenohypophysis, tests for side effects and toxicity of pharmaceutical products, and the development of a new therapeutic method for diseases of adenohypophysis and the like. For example, iPS cells are produced from a human patient with the aforementioned disease resulting from a disorder of adenohypophysis, particularly a hereditary disease resulting from a disorder of adenohypophysis and, using the iPS cells, a cell aggregate containing adenohypophysis or a precursor tissue thereof is produced by the method of the present invention. The adenohypophysis or precursor tissue thereof contained in the obtained cell aggregate may reproduce the disorder of adenohypophysis causing the disease of the patient in vitro. The cell aggregate containing the disordered adenohypophysis or a precursor tissue thereof, or disordered adenohypophysis or precursor tissue thereof isolated therefrom is cultivated in the presence or absence (negative control) of a test substance. Then, the level of disorder of the cell aggregate, adenohypophysis or precursor tissue thereof treated with the test substance is compared with that of the negative control. As a result, a test substance that reduced the level of the disorder can be selected as a candidate substance for a therapeutic drug for the disease resulting from the disorder. In addition, by administering a therapeutically effective amount of a substance selected by using, as a test substance, a substance having confirmed safety as a medicament, to a patient who is the origin of the cell aggregate, or adenohypophysis or a precursor tissue thereof, used for screening, a disease resulting from a disorder of adenohypophysis in the patient can be treated. Furthermore, using a cell aggregate containing the disordered adenohypophysis or a precursor tissue thereof, or disordered adenohypophysis or a precursor tissue thereof isolated therefrom, side effect, toxicity tests of a pharmaceutical product and the development of a new treatment method for a disease resulting from the disorder can be performed.

The present invention is more specifically explained by referring to the following Examples. The Examples are mere exemplification of the present invention and do not limit the scope of the present invention.

EXAMPLES

[Example 1] Steric Formation of Ventral Hypothalamus and Epidermal Placode from Human Pluripotent Stem Cells (Method)

Human ES cells (KhES-1) were subjected to maintenance culture by a conventional method on MEF and used. To monitor differentiation induction into a hypothalamus tissue, KhES-1 wherein Venus cDNA is knocked-in into the gene of Rx which is a hypothalamus neuroepithelium marker was used. To differentiate human ES cells by serum-free suspension culture of aggregate (SFEBq method), human ES cells were dispersed to single cells by enzyme by the method of Nakano et al. (Cell Stem Cell, 2012), and reaggregated in a low cell adhesive V-bottom 96 well plate (SUMITOMO BAKELITE). 5,000 cells were seeded per well, and cultured in the following differentiation medium at 5% $CO_2$, 37° C. gfCDM medium (growth-factor-free Chemically Defined Medium; Wataya et al., PNAS, 2008)+5% KSR (Invitrogen).

With the day of seeding as day 0 of differentiation culture, 20 μM Y-27632 (ROCK inhibitor; inhibitor of cell death during dispersion: Watanabe et al., Nature Biotechnology, 2007) was added from day 0 to day 3, and a half of the medium was exchanged with a differentiation medium free of Y-27632 on days 3 and 6 of culture. From day 3 to day 18 of culture, BMP4 (final concentration 5 nM) was added to the medium. On and after day 18, a half of the medium was exchanged every 3 days with a medium free of BMP4. On and after day 6 of culture, SAG (final concentration 2 μM) was added to of the medium. On and after day 18, the oxygen partial pressure during the culture was set to 40%. Tissue differentiation was analyzed by a fluorescent antibody method.

(Results)

The inside of the aggregate of human ES cells cultured by the above-mentioned method was largely occupied by Rx::Venus-positive, Chx10 (retina marker)-negative hypothalamus neuroepithelial tissues on day 17 of differentiation culture, whereas E-cadherin-positive surface ectoderm formed a single cell layer on the surface (FIG. 1A). On day 24 of culture, most part of Rx::Venus-positive hypothalamus expressed Nkx2.1, which is a ventral hypothalamus marker (FIG. 1B). While the surface ectoderm expressed pan-cytokeratin which is a surface ectoderm (including oral ectoderm) marker, a part thereof was thickened and showed a form of epidermal placode (including hypophysial placode) (FIG. 1C).

[Example 2] Differentiation of Hypophysial Placode and Self Organization of Rathke's Pouch (Method)

The cell aggregates derived from human ES cells and simultaneously containing ventral hypothalamus tissue and epidermal placode were formed by the method of Example 1, culture was continued until day 27 or day 30 of culture under similar conditions, and the aggregates were analyzed by a fluorescent antibody method. In some culture, FGF2 (final concentration 20 ng/ml) was added to the medium from day 15 of culture.

(Results)

Figure 2:
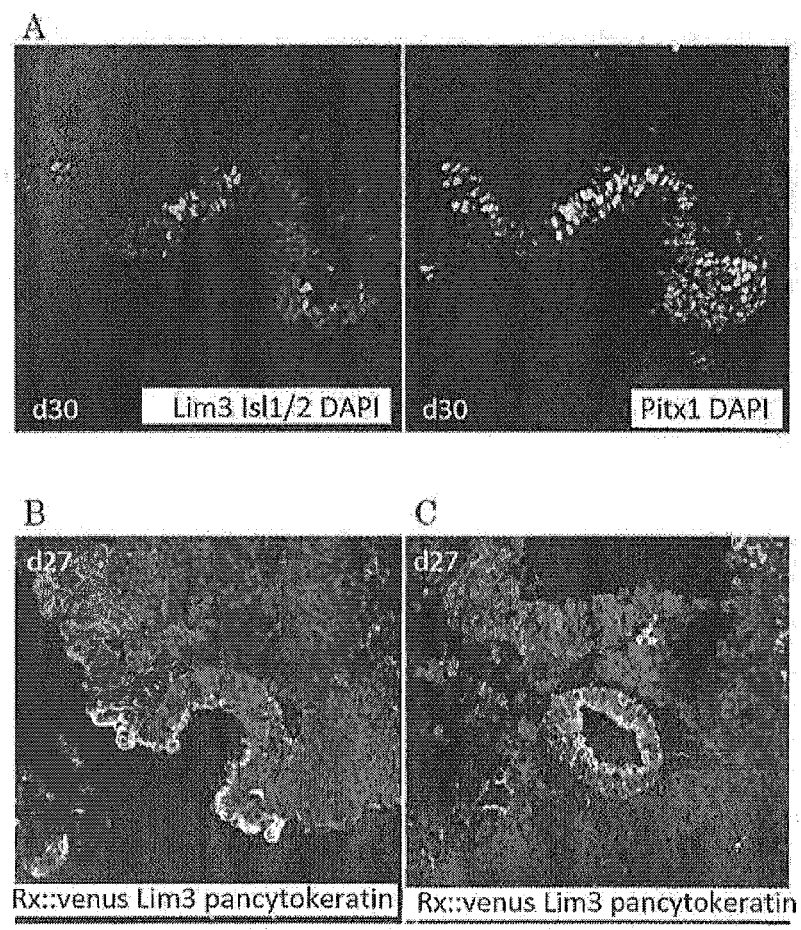
FIG. 2 shows differentiation of hypophysial placode and self organization of Rathke's pouch. A: d30 aggregate. Left figure, Lim3: green, Isl1/2: red, DAPI: blue. Right figure, Pitx1: white, DAPI: blue. B: d27 aggregate. Rx::Venus: green, Lim3: red, pan-cytokeratin: white. C: d27 aggregate. Rx::Venus: green, Lim3: red, pan-cytokeratin: white.

On day 27 and day 30 of culture, the pan-cytokeratin-positive epidermal placode was markedly thickened and, in the analysis by a fluorescent antibody method, strongly expressed hypophysis progenitor cell markers such as Lim3, Pitx1 and Isl1/2 and the like (FIG. 2A). A part of the thickened placode expressing these markers was invaginated toward the inside, as in initial formation of fetal Rathke's pouch (FIG. 2B), and other part formed cyst (FIG. 2C). The addition of FGF2 increased formation of hypophysial placode by 30%.

[Example 3] Role of BMP4 in Differentiation Induction of Hypophysial Placode (Method)

By the method of Example 1, an influence of the presence or absence of BMP4 addition on the differentiation of cell aggregates was analyzed by a fluorescent antibody method.

(Results)

Figure 3:
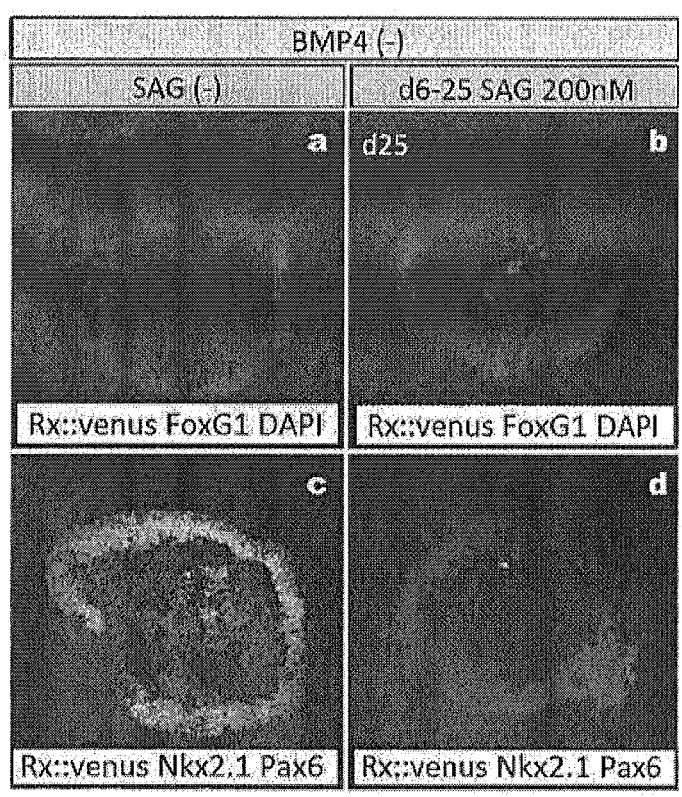
FIG. 3 shows differentiation induction under BMP4 non-addition conditions. Photographs of d24 or 25 aggregates. a and c: SAG free. b and d: d6-25, SAG (200 nM). a and b: Rx::Venus: green, FoxG1: red, DAPI: blue. c and d: Rx::Venus: green, Nkx2.1: red, Pax6: white.

When BMP4 was not added, surface ectoderm was not formed on the surface of the aggregate on day 24 of culture, and neuroepithelium occupied the whole surface. It was found that most of the neuroepithelium did not express Rx::Venus, was FoxG1-positive and formed a cerebrum tissue (FIG. 3a, b). When SAG was not added, FoxG1-positive and Pax6-positive cerebral cortex were differentiated and when SAG was added, FoxG1-positive and Nkx2.1-positive basal ganglion was differentiated (FIG. 3a-d). Thus, suspension aggregate culture of human pluripotent stem cells has clarified that exogenous BMP4 simultaneously plays two roles of 1) active formation of surface ectoderm and 2) differentiation induction of neural tissue of hypothalamus (essential for induction of hypophysial placode) rather than cerebrum.

[Example 4] Role of Hedgehog Signal in Differentiation Induction of Hypophysial Placode (Method)

By the method of Example 1, an influence of the presence or absence of the addition of hedgehog signal agonist SAG on the differentiation of cell aggregate was analyzed by a fluorescent antibody method.

(Results)

Figure 4:
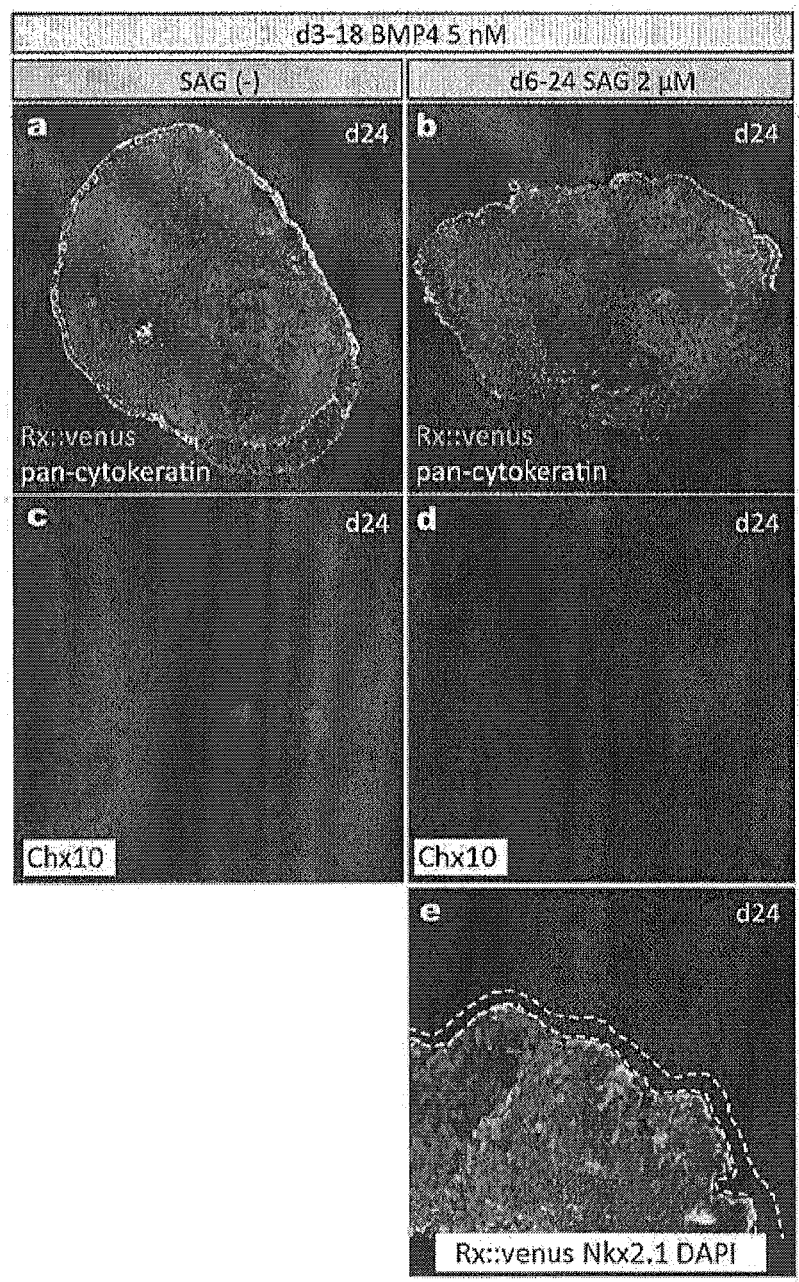
FIG. 4 shows the role of hedgehog signal in induction of differentiation of hypophysial placode. Photographs of d24 aggregates. a and c: SAG free. b, d and e: d6-25, SAG (2 µM). a and b: Rx::Venus: green, pan-cytokeratin: white. c and d: chx10: red. e: Rx::Venus: green, Nkx2.1: red, DAPI: blue.

With or without addition of SAG, surface ectoderm was formed on the surface of the aggregates on day 24 and day 27 of culture, and Rx::Venus-positive tissues occupied the whole inside thereof (FIG. 4a, b). When SAG was added from day 6 of culture, ventral hypothalamus tissue (Rx::Venus-positive, Chx10-negative, Nkx2.1-positive) was formed in the inside of the aggregates as in Examples 1, 2, and hypophysial placode was formed on the surface (FIG. 4b, d, e). On the other hand, when SAG was not added, neural retinal tissue (Rx::Venus-positive, Chx10-positive, Nkx2.1-negative) was formed in the inside, and formation of hypophysial placode was not observed on the surface (FIG. 4a, c). Thus, it was clarified that ventral hypothalamus rather than neural retina can be efficiency formed by allowing a strong hedgehog signal to act at a right timing.

[Example 5] Induction of Differentiation of ACTH-Producing Endocrine Cells from Hypophysial Placode (Method)

In the same manner as in Examples 1, 2, hypophysial placode was self-organized by suspension aggregate culture of human ES cells. From day 30 of culture, the aggregates were transferred to EZ Sphere plate, suspension culture was continued at 40% $O_2$, 5% $CO_2$, 37° C. From day 30 to day 45 of culture, gfCDM+10% KSR supplemented with SAG (2 µM), FGF2 (20 ng/ml) was used as the medium. On and after day 45 of culture, a similar medium having a KSR concentration increased to 20% was used for culture. Differentiation of endocrine cells was analyzed by a fluorescence method.

(Results)

Figure 5:
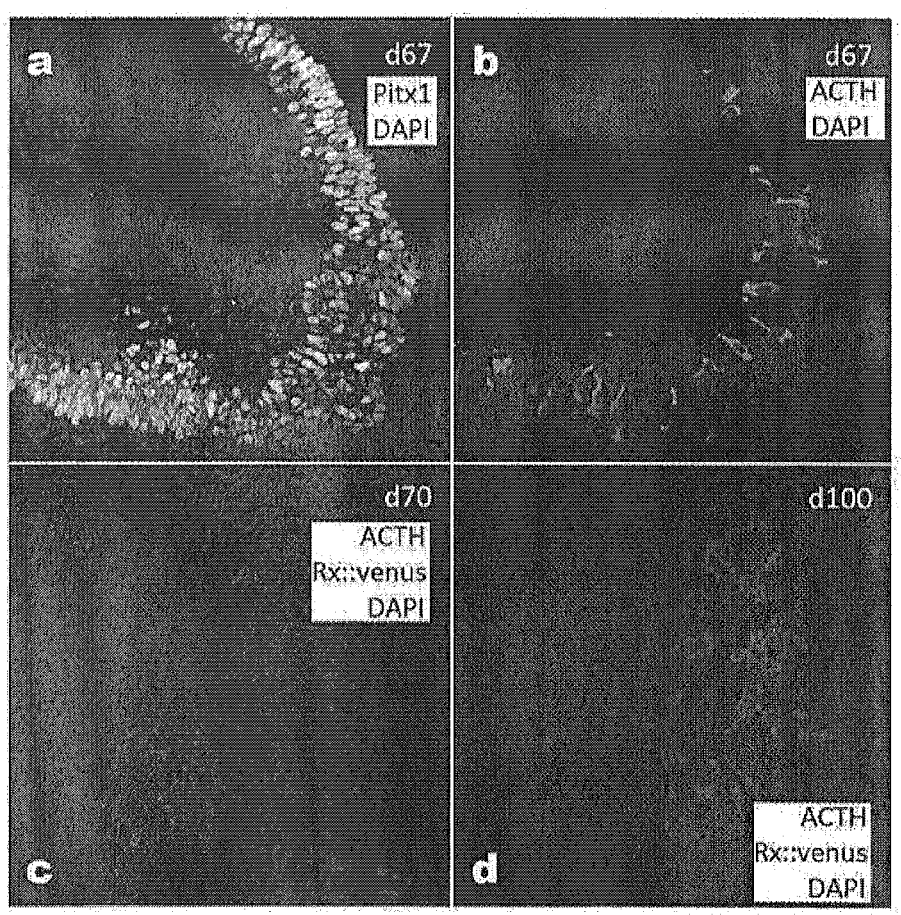
FIG. 5 shows induction of differentiation of ACTH-producing endocrine cells from hypophysial placode. a: d67 aggregate. Pitx1: white, DAPI: blue. b: d67 aggregate. ACTH: green, DAPI: blue. c: d70 aggregate. Rx::Venus: green, ACTH: red, DAPI: blue. d: d100 aggregate. Rx::Venus: green, ACTH: red, DAPI: blue.

In the samples on day 67 of culture, many ACTH-producing cells were confirmed in Pitx1-positive hypophysis tissue by a fluorescent antibody method (FIG. 5a, b). Similar ACTH-positive cells were also confirmed in the samples on day 70 and day 100 of culture (FIG. 5c, d).

[Example 6] Induction of ACTH Release, by CRH, from Hypophysis Endocrine Cells Derived from Human Pluripotent Stem Cells (Method)

In vitro hormone secretory capacity was analyzed using the aggregates containing ACTH-producing cells produced by the method of Example 5. Using a 1.5 ml Eppendorf tube containing 250 µl of HBSS(−) containing 16 aggregates at day 80 of culture, the aggregates were incubated in the presence or absence of CRH (1 µg/ml) at 37° C. for 10 min. The concentration of ACTH in the culture supernatant was quantified by the ELISA method.

Furthermore, to examine feedback suppressive ability due to downstream hormone (glucocorticoid), 16 aggregates on day 80 of culture were preincubated in the presence or absence of hydrocortisone (20 µg/ml) at 37° C. for 3 hr, and the effect of release of ACTH after CRH treatment was analyzed.

(Results)

Figure 6:
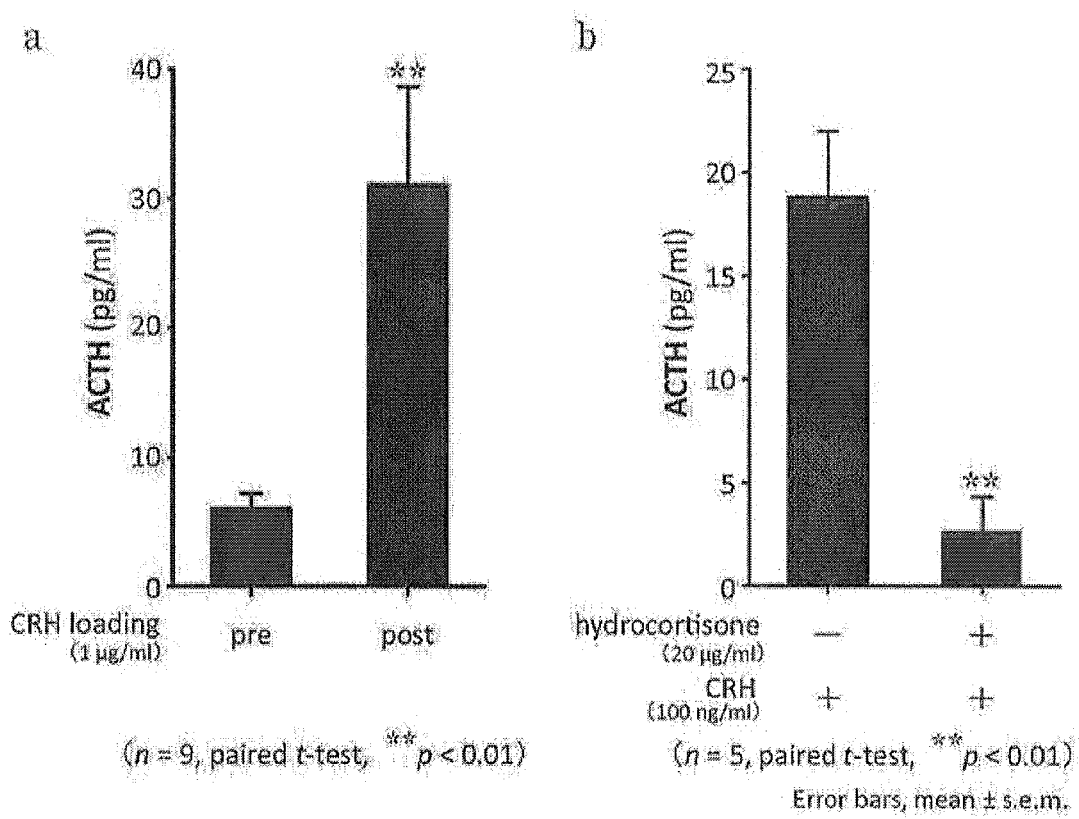
FIG. 6 shows induction, by CRH, of the release of ACTH from hypophysis endocrine cells derived from human pluripotent stem cells. a: Concentration (pg/ml) of ATCH in the culture supernatant upon CRH stimulation. b: Effect of hydrocortisone on the concentration (pg/ml) of ATCH in the culture supernatant.

In the culture supernatant after incubation in the presence of CRH (1 µg/ml), ACTH was secreted at not less than 5-fold concentration as compared to the culture supernatant after incubation in the absence of CRF (FIG. 6a).

In the group with preincubation in the presence of hydrocortisone (20 µg/ml), the ACTH concentration decreased to less than one-sevenths of that of the group with preincubation in the absence thereof (FIG. 6b).

[Example 7] Secretion of ACTH and Corticosteroid In Vivo by CRH from ACTH-Producing Cells Derived from ES Cells (Method)

Aggregates of ACTH-producing cells differentiated from human ES cells by the method of Example 5 (except that Fgf2 was not added) was transplanted under the kidney capsule of hypophysectomized mouse. It was confirmed before transplantation that these mice lost ACTH secretory capacity by performing a CRH loading test after hypophysectomy.

To be specific, the aggregates were cultured for 72 to 82 days, hypophysial placode containing ACTH-producing cells was excised from the aggregates and transplanted with a microsyringe under the kidney capsule of a hypophysectomied mouse. At 14 days after the transplantation, CRH loading test was performed, and plasma ACTH value before the loading and plasma ACTH and corticosteroid (corticosterone) value after the loading were measured by the ELISA method.

(Results)

Figure 7:
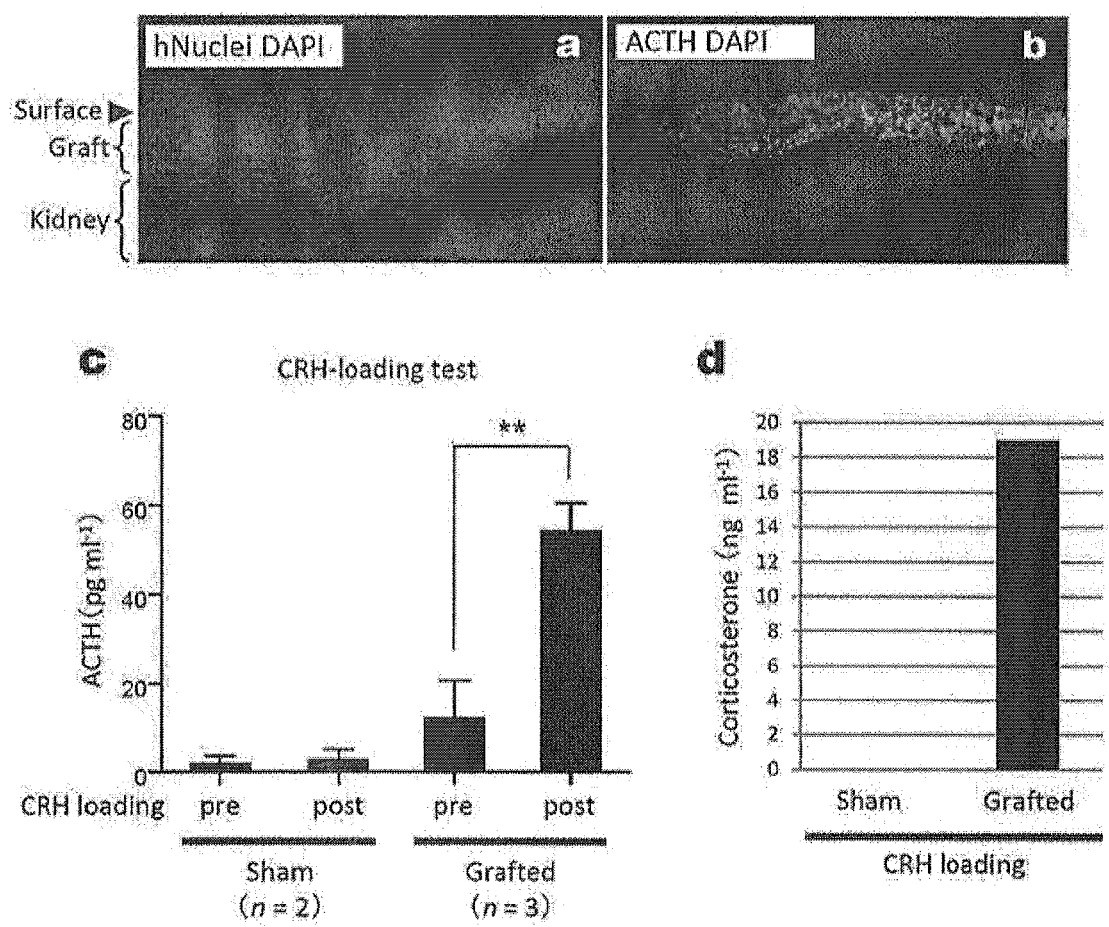
FIG. 7 shows in vivo secretion, by CRH, of ACTH and corticosteroid from ACTH-producing cells derived from human ES cells. a: ACTH-producing cells at 14 days after transplantation. hNuclei: red, DAPI: blue. b: ACTH-producing cells at 14 days after transplantation. ACTH: green, DAPI: blue. c: ACTH concentration in plasma following CHR loading. The error bar shows mean±s.e.m. **$P<0.01$, paired t-test. d: Corticosterone concentration in plasma following CHR loading.

It was found by a fluorescent antibody method that ES cell-derived ACTH-producing cells transplanted under the kidney capsule were engrafted even 14 days after the transplantation (FIG. 7a, b). In the control group (Sham operation), plasma ACTH value was less than 3 pg/ml, and the corticosterone value was less than 0.2 ng/ml even after CRH loading. On the other hand, in the transplantation group, ACTH value was 50-60 pg/ml, and the corticosterone value was 19 ng/ml after CRH loading (FIG. 7c, d). Also, in the transplantation group, ACTH value after CRH loading was not less than 4-fold of the ACTH value before the loading (FIG. 7c).

[Example 8] Improvement of Activity, Survival and Body Weight Decrease in Hypophysectomied Mouse by Transplantation of ACTH-Producing Cells Derived from ES Cells (Method)

ACTH-producing cells derived from human ES cells were transplanted under the kidney capsule of hypophysectomied mouse (9-week-old) as in Example 7. The survival and body weight change of the transplanted mouse was observed with time, and the locomotion of the mouse was also evaluated in comparison with the control group (sham operation). As for the locomotion of mouse, how many times the mouse spontaneously rotated the running wheel per day was measured using ENV-044 (MedAssociates, Georgia) (Running wheel activity test). In addition, using an IR sensor (MDC-W02 (Brain Science Idea, Osaka)), the distance of spontaneous movement of the mouse in the cage was also measured (Home-cage activity test).

(Results)

Figure 8:
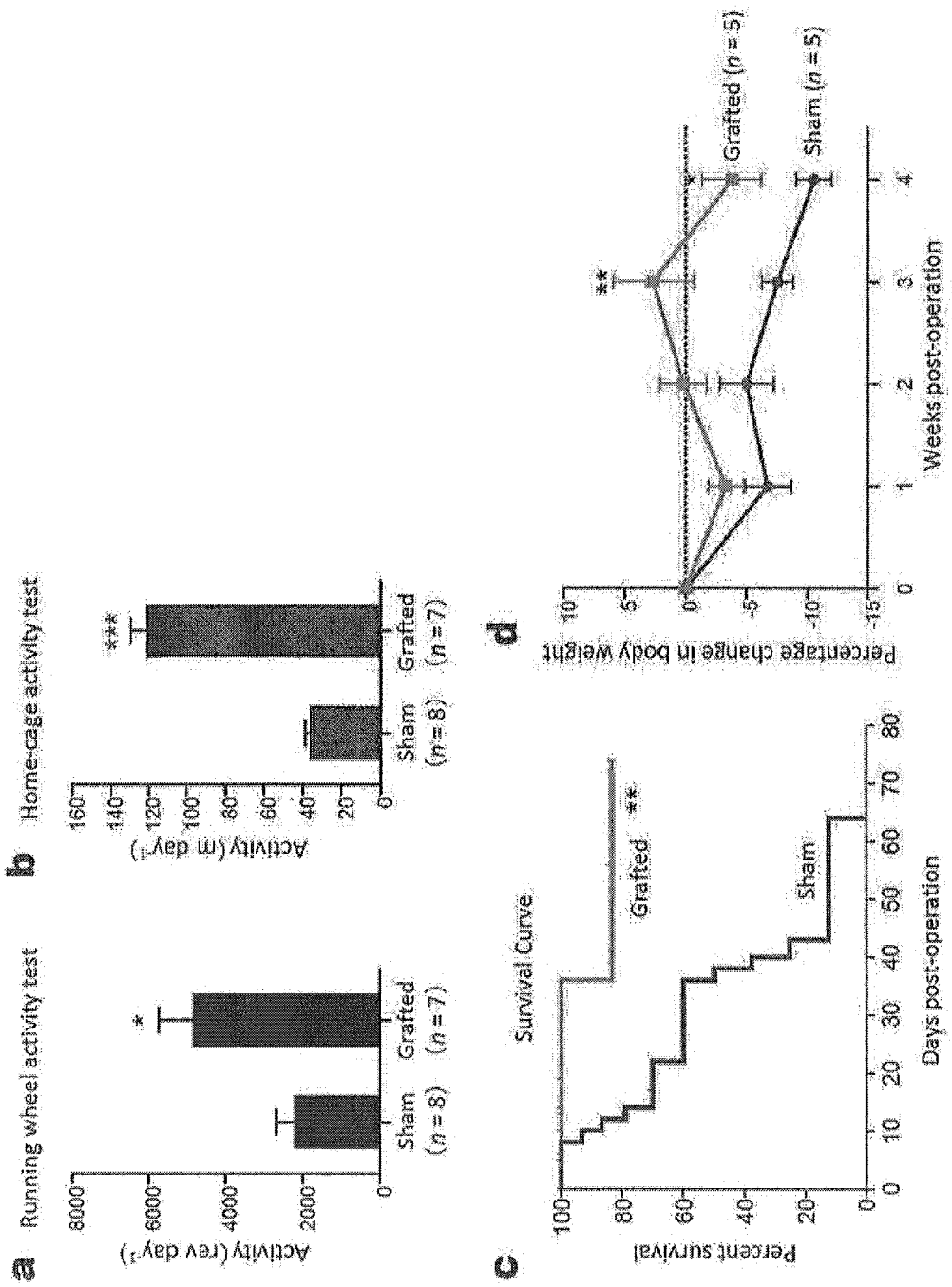
FIG. 8 shows improvements of the activity, survival and body weight decrease of hypophysectomied mouse by transplantation of ACTH-producing cells derived from human ES cells. a: shows the results of a running wheel activity test. b: shows the results of a home-cage activity test. c: shows improvement of survival by transplantation of ACTH-producing cells. d: shows improvement of body weight decrease by transplantation of ACTH-producing cells. The error bar shows mean±s.e.m. *$P<0.05$, $P<0.01$, *$P<0.001$. Student's t-test (a, b), log-rank test (c), Mann-Whitney test (d).

The mouse of the transplantation group showed high level of locomotion as compared to the control group (FIG. 8a, b).

In the control group, all mice died by 64 days after the sham operation, whereas 83% of the mice survived in the transplantation group (FIG. 8c). Furthermore, the transplantation group hardly showed a body weight decrease in 3 and 4 weeks after operation as compared to the control group (FIG. 8d).

[Example 9] Promotion of Differentiation Induction of ACTH-Producing Endocrine Cells by Notch Signal Inhibitor (Method)

According to the method of Example 5, hypophysial placode derived from human ES cells was formed, and cultured for a long term. DAPT (10 µM), a Notch signal inhibitor, was allowed to act thereon from day 65 to day 74 of culture, and the effect thereof was analyzed by a qPCR method.

(Results)

Figure 9:
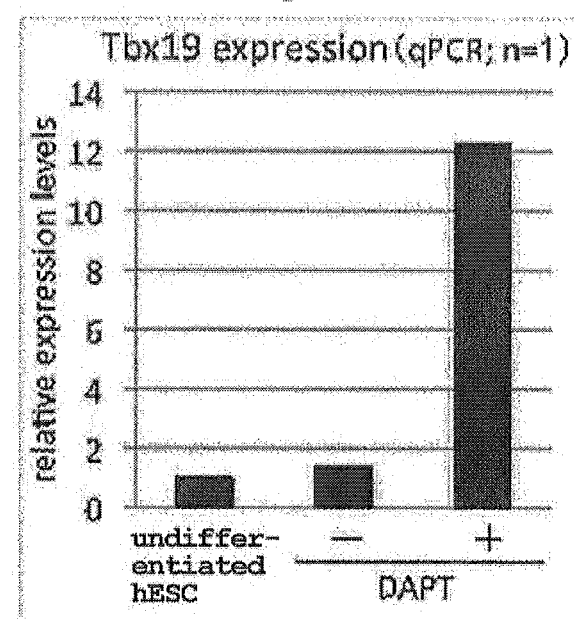
FIG. 9 shows induction of Tbx19 expression in the aggregates by DAPT treatment.

By comparison of the DAPT treatment group and non-treatment group by a qPCR method, expression of transcription factor Tbx19 which is a marker of ACTH-producing cells and controls upstream of ACTH production increased 8 times or more in the treatment group in the aggregates on day 74 of culture (FIG. 9).

[Example 10] Induction of Differentiation of GH- and PRL-Producing Endocrine Cells from Hypophysial Placode (Method)

According to the method of Example 5, hypophysial placode derived from human ES cells was formed, and cultured for a long term. On day 67 or 70 of culture, differentiation of the endocrine cells was analyzed by a fluorescent antibody method.

(Results)

Figure 10:
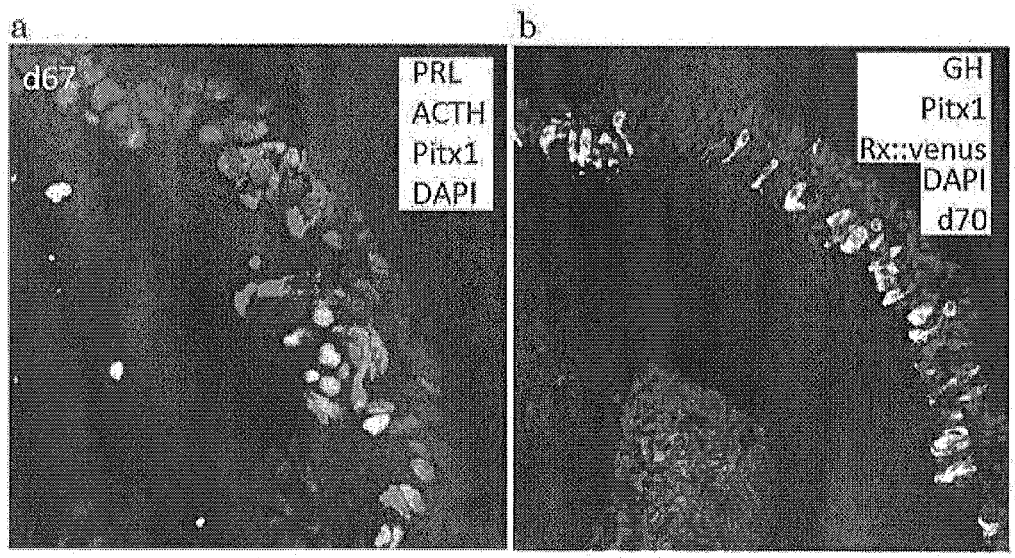
FIG. 10 shows induction of differentiation of GH- and PRL-producing endocrine cells from hypophysial placode. a: d67 aggregate. PRL: green, ACTH: red, Pitx1: white, DAPI: blue. b: d70 aggregate. Rx::Venus: green, Pitx1: red, GH: white, DAPI: blue.

As a result of the analysis of Pitx1-positive hypophysial placode on day 67 of culture, PRL-producing cells were found in addition to ACTH-producing cells (FIG. 10a). As a result of the analysis of Pitx1-positive hypophysial placode on day 70 of culture, many GH-producing cells were also detected (FIG. 10b).

[Example 11] Steric Formation of Dorsal Hypothalamus from Human Pluripotent Stem Cells (Method)

Until 6 days after the differentiation induction, the cells were cultured under culture conditions of Example 1 and, on and after day 6, a half of the medium was exchanged every 3 days with a medium free of BMP4. SAG (final concentration 1 µM) was added to the medium from day 6 to day 12. On and after day 18, the oxygen partial pressure during the culture was set to 40%. Tissue differentiation was analyzed by a fluorescent antibody method.

(Results)

Figure 11:
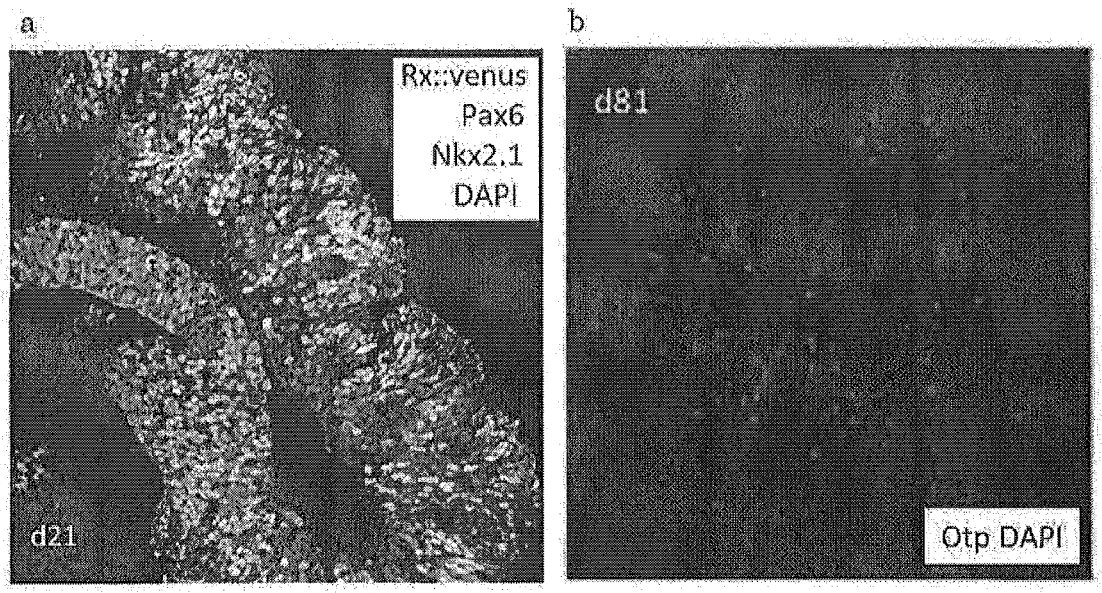
FIG. 11 shows steric formation of dorsal hypothalamus from human pluripotent stem cells. a: d21 aggregate. Rx::Venus: green, Nkx2.1: red, Pax6: white, DAPI: blue. a: d81 aggregate. Otp: red, DAPI: blue.

In the inside of the aggregate of human ES cells cultured by the above-mentioned method, neuroepithelium of dorsal hypothalamus (Rx::venus-positive, Pax6-positive, Chx10-negative) was observed together with ventral hypothalamus tissue (Rx::venus-positive, Nkx2.1-positive, Chx10-negative) on day 24 of differentiation culture (FIG. 11a). On day 81 of differentiation culture, expression of Otp, a late marker of dorsal hypothalamus, was also found (FIG. 11b). Thus, it was clarified that the dorsal hypothalamus can be efficiently formed by shortening the period of action of the BMP4 than in the differentiation conditions of Example 1 and further decreasing the concentration of SAG.

[Example 12] Induction of GH Release from Hypophysis Endocrine Cells Derived from Human Pluripotent Stem Cells by GRF (Method)

In addition to the method of Example 10, in vitro hormone secretory capacity was analyzed using the aggregate containing GH-producing cells differentiated in a medium containing hydrocortisone (1 µg/ml) from days 72 to 84 of culture. Using a 1.5 ml Eppendorf tube containing 500 µl of HBSS containing 33 aggregates at day 84 of culture, the aggregates were incubated in the presence or absence of GRF (100 ng/ml) at 37° C. for 30 min. The concentration of GH in the culture supernatant was quantified by the ELISA method.

(Results)

Figure 12:
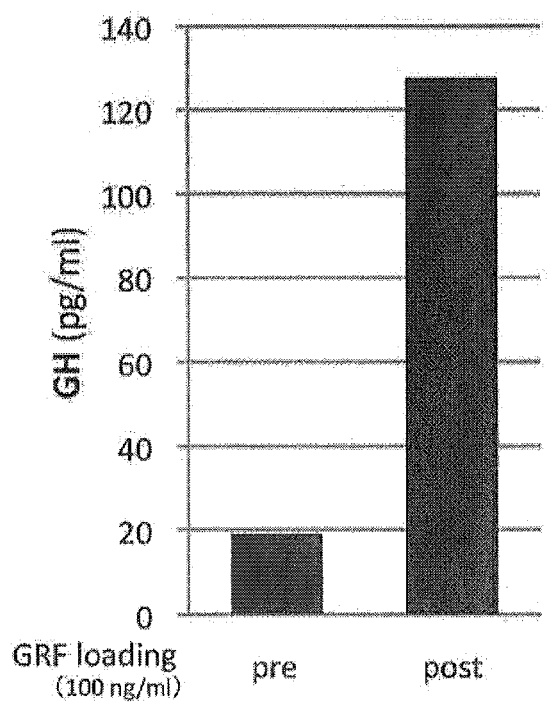
FIG. 12 shows induction, by GRF, of the release of GH from hypophysis endocrine cells derived from human pluripotent stem cells. The vertical axis shows GH concentration (pg/ml) of the culture supernatant.

In the culture supernatant after incubation in the presence of GRF, GH was secreted at not less than 6-fold concentration as compared to the culture supernatant after incubation in the absence of GRF (FIG. 12).

[Example 13] Induction of GH Release by GRF from GH-Producing Cells Induced by Dexamethasone (Method)

In addition to the method of Example 10, in vitro hormone secretory capacity was analyzed using the aggregate containing GH-producing cells differentiated in a medium containing dexamethasone (40 ng/ml) from days 70 to 84 of culture. Using a 1.5 ml Eppendorf tube containing 750 µl of a medium containing 30 aggregates at day 84 of culture, the aggregates were incubated in the presence of GRF (0.1, 1, 10 µg/ml) at 37° C. for 30 min. The concentration of GH in the culture supernatant was quantified by the ELISA method. In addition, in order to investigate a potential of somatostatin to suppress GH secretion, 18 aggregates at day 98 of culture were incubated in the presence or absence of somatostatin (100 ng/ml) at 37° C. for 90 min, and effects on GH release after GRF treatment were analyzed.

(Results)

When dexamethasone was not added to the differentiation medium, the concentration of GH in the culture supernatant was extremely low even when incubated with GRF. In contrast, when dexamethasone was added, GH secretion was found in the culture supernatant in response to GRF (FIG. 13a).

Figure 13:
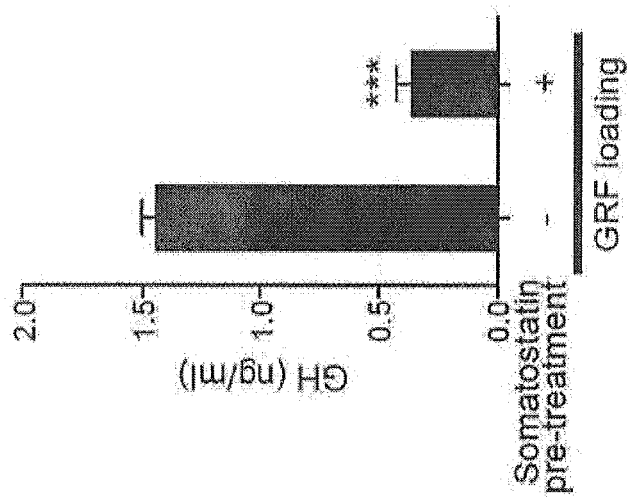
FIG. 13 shows induction of GH-producing cells by dexamethasone. (a) shows induction of GH release by GRF from GH-producing cells induced by dexamethasone. n=3, one-way ANOVA, *$p<0.05$, *$p<0.001$. (b) shows effect of somatostatin treatment on GH release. n=3, Student's t-test, *$p<0.001$.
Figure 13:
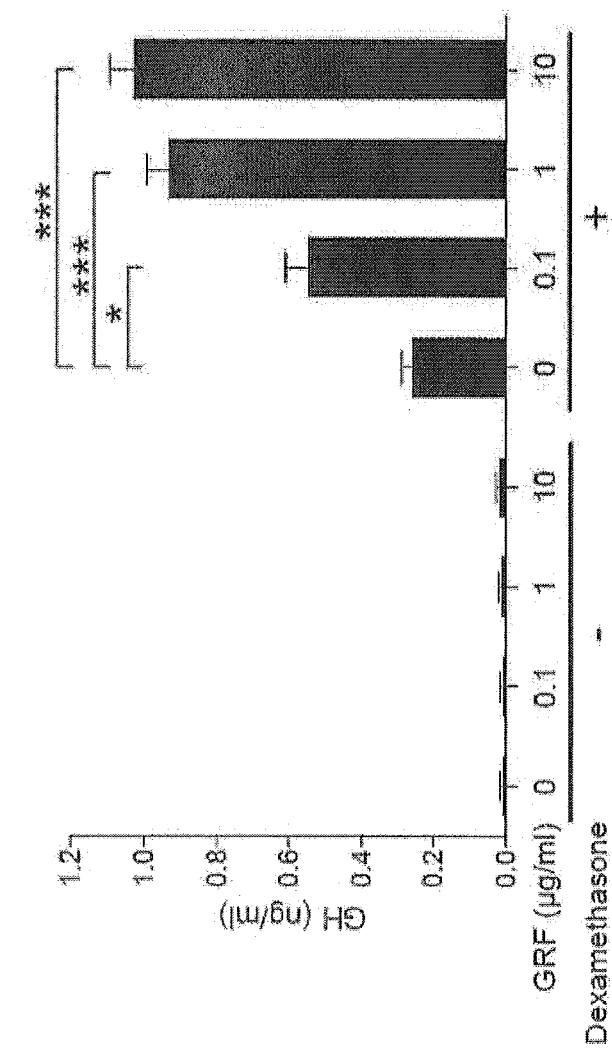

In the group preincubated in the presence of somatostatin (100 ng/ml), the GH concentration decreased to about one-fourth as compared to that in the group preincubated in the absence of somatostatin (FIG. 13b)

[Example 14] Differentiation Induction of TSH-Producing Endocrine Cells from Hypophysial Placode (Method)

Differentiation of the endocrine cells cultured for 84 days according to the method of Example 13 was analyzed by a fluorescent antibody method.

(Results)

Figure 14:
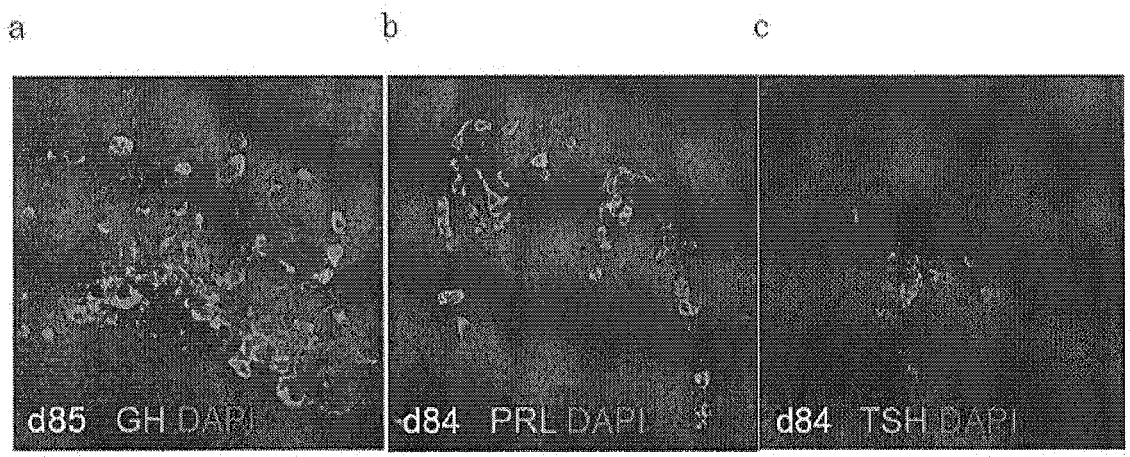
FIG. 14 shows induction of endocrine cells from hypophysial placode. a: GH-producing cells, b: PRL-producing cells, c: TSH-producing cells.

As a result of the analysis of hypophysial placode on day 84 of culture, TSH-producing cells were found in addition to GH-, PRL-producing cells (FIG. 14a-c).

[Example 15] Differentiation Induction of LH/FSH-Producing Endocrine Cells from Hypophysial Placode (Method)

In addition to the method of Example 8, differentiation of hypophysial placode reacted with Notch signal inhibitor DAPT (10 µM) from day 72 to day 82 of culture was analyzed by a fluorescent antibody method.

(Results)

Figure 15:
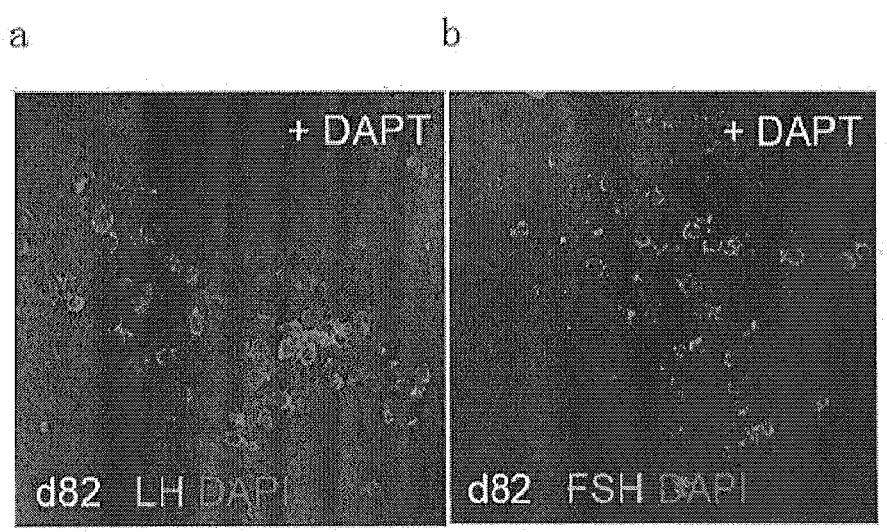
FIG. 15 shows induction of endocrine cells from hypophysial placode. a: LH-producing cells, b: FSH-producing cells.

LH-producing cells and FSH-producing cells were found in the hypophysial placode (FIG. 15a, b).

INDUSTRIAL APPLICABILITY

According to the present invention, adenohypophysis or a precursor tissue thereof can be efficiently induced in vitro from human pluripotent stem cells. Both the hypothalamus neuroepithelial tissue and surface ectoderm are simultaneously formed in the aggregates of human pluripotent stem cells, and hypophysial placode and Rathke's pouch are self organized by the interactions thereof. According to the present invention, in the same manner as the hypophysis in a body, human adenohypophysis having an ability to regulate secretion of pituitary hormone in response to stimulation of the hypothalamus and regulation of feedback from the downstream target tissue can be constructed in vitro.

The contents disclosed in any publication cited herein, including patents and patent applications, are hereby incorporated in their entireties by reference, to the extent that they have been disclosed herein.

This application is based on a patent application No. 2014-152384 filed in Japan (filing date: Jul. 25, 2014), the contents of which are incorporated in full herein.

The invention claimed is:

1. A method for producing a human cell aggregate comprising an adenohypophysis or a precursor tissue thereof, which comprises the steps of:
   (a) culturing an aggregate of human pluripotent stem cells in suspension in a medium containing a bone morphogenetic protein signal transduction pathway activating substance and a substance acting on the Shh signal pathway that enhances signal transduction mediated by Shh to obtain a human cell aggregate comprising a hypothalamus neuroepithelial tissue and a surface ectoderm,
   (b) culturing the obtained human cell aggregate comprising the hypothalamus neuroepithelial tissue and the surface ectoderm in suspension in a medium containing a bone morphogenetic protein signal transduction pathway activating substance and a substance acting on the Shh signal pathway that enhances signal transduction mediated by Shh to induce formation of hypophysial placode and/or Rathke's pouch in the surface ectoderm, wherein the concentration of the bone morphogenetic protein signal transduction pathway activating substance is reduced by medium exchanges, thereby obtaining a human cell aggregate comprising (i) hypothalamus neuroepithelial tissue and (ii) hypophysial placode and/or Rathke's pouch, and
   (c) culturing the human cell aggregate comprising (i) hypothalamus neuroepithelial tissue and (ii) hypophysial placode and/or Rathke's pouch in suspension in a medium comprising a substance acting on the Shh signal pathway that enhances signal transduction mediated by Shh to induce differentiation of hypophysial placode and/or Rathke's pouch into pituitary hormone-producing cells, thereby obtaining a human cell aggregate comprising an adenohypophysis.

2. The production method according to claim 1, wherein the medium used in step (b) further comprises FGF2.

3. The production method according to claim 1, wherein the medium used in step (c) further comprises FGF2.

4. The production method according to claim 1, wherein the medium used in step (c) further comprises a Notch signal inhibitor.

5. The production method according to claim 4, wherein the Notch signal inhibitor is DAPT.

6. The production method according to claim 1, wherein the pituitary hormone-producing cells are at least one selected from the group consisting of growth hormone (GH)-producing cells, prolactin (PRL)-producing cells, and adrenocorticotropic hormone (ACTH)-producing cells.

7. The production method according to claim 1, wherein the bone morphogenetic protein signal transduction pathway activating substance is BMP4.

8. The production method according to claim 1, wherein the substance acting on the Shh signal pathway is SAG.

9. The production method according to claim 1, wherein the hypothalamus neuroepithelial tissue is a ventral hypothalamus neuroepithelial tissue.

10. The production method according to claim 1, wherein the pluripotent stem cells are embryonic stem cells or induced pluripotent stem cells.

11. The production method according to claim 1, wherein the culturing in suspension is performed in the absence of feeder cells.

12. A cell aggregate obtainable by the production method according to claim 1.

13. The production method according to claim 2, wherein the medium used in step (c) further comprises FGF2.

14. The production method according to claim 2, wherein the medium used in step (c) further comprises a Notch signal inhibitor.

15. The production method according to claim 2, wherein the pituitary hormone-producing cells are at least one kind selected from the group consisting of growth hormone (GH)-producing cells, prolactin (PRL)-producing cells, and adrenocorticotropic hormone (ACTH)-producing cells.

16. The production method according to claim 1, wherein step (b) is performed for not less than 6 days, and wherein the concentration of the bone morphogenetic protein signal transduction pathway activating substance in step (b) is reduced by half every 2-4 days or is reduced to not more than ¼ compared to that at the start of step (b).

17. The production method according to claim 1, wherein culturing in step (b) is performed under oxygen partial pressure of 30-60%.

18. The production method according to claim 1, wherein the medium used in step (c) is not supplemented with a bone morphogenetic protein signal transduction pathway activating substance.

19. The production method according to claim 1, wherein the pituitary hormone-producing cells are at least two kinds of pituitary hormone-producing cells selected from the group consisting of growth hormone (GH)-producing cell, prolactin (PRL)-producing cell, and adrenocorticotropic hormone (ACTH)-producing cell.

* * * * *